United States Patent
Charlebois et al.

(10) Patent No.: US 9,956,384 B2
(45) Date of Patent: May 1, 2018

(54) ARTICULATING BALLOON CATHETER AND METHOD FOR USING THE SAME

(71) Applicant: Cook Medical Technologies LLC, Bloomington, IN (US)

(72) Inventors: Steven Charlebois, West Lafayette, IN (US); Sara Sherman, Lafayette, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 453 days.

(21) Appl. No.: 14/603,515

(22) Filed: Jan. 23, 2015

(65) Prior Publication Data

US 2015/0209558 A1    Jul. 30, 2015

Related U.S. Application Data

(60) Provisional application No. 61/930,988, filed on Jan. 24, 2014.

(51) Int. Cl.
*A61M 25/10*  (2013.01)
*A61M 25/01*  (2006.01)

(52) U.S. Cl.
CPC .... *A61M 25/1011* (2013.01); *A61M 25/0155* (2013.01); *A61M 25/1002* (2013.01);
(Continued)

(58) Field of Classification Search
CPC .......... A61M 25/1011; A61M 25/0155; A61M 25/1002; A61M 25/1025;
(Continued)

(56) References Cited

U.S. PATENT DOCUMENTS 2,233,554 A    3/1941    Pletcher
3,173,418 A    3/1965    Baran
(Continued)

FOREIGN PATENT DOCUMENTS

CN    102600546    7/2012
DE    4225553    5/1994
(Continued)

OTHER PUBLICATIONS

Woodson et al. Multicenter study of a novel adjustable tongue-advacement device for obstructive sleep apnea [article]. Otolaryngology—head and neck surgery, vol. 143, No. 4, pp. 585-590. IP: 128.210.125.135. Jun. 10, 2010. SAGE.
(Continued)

*Primary Examiner* — Manuel Mendez
(74) *Attorney, Agent, or Firm* — Buchanan Van Tuinen LLC

(57) ABSTRACT

Articulating balloon catheters and methods of using articulating balloon catheters are described herein. An embodiment of an articulating balloon catheter comprises an elongate member and a balloon. The balloon is attached to the elongate member and is adapted to move between a deflated configuration and an inflated configuration. The balloon has a proximal portion, a distal portion, and an articulating region disposed between the proximal portion and the distal portion. The articulating region of the balloon is configured to provide articulation between the proximal portion and the distal portion of the balloon.

20 Claims, 7 Drawing Sheets

(52) U.S. Cl.
CPC ... *A61M 25/1025* (2013.01); *A61M 2025/105* (2013.01); *A61M 2025/1013* (2013.01); *A61M 2025/1045* (2013.01); *A61M 2025/1086* (2013.01); *A61M 2025/1088* (2013.01); *A61M 2025/1093* (2013.01)

(58) Field of Classification Search
CPC .. A61M 2025/1013; A61M 2025/1045; A61M 2025/105; A61M 2025/1086; A61M 2025/1088; A61M 2025/1093
USPC .............. 606/191–194; 604/96.01, 101.02, 604/103.01–103.14, 916
See application file for complete search history.

(56) References Cited

U.S. PATENT DOCUMENTS

| | | |
|---|---|---|
| 3,598,120 A | 8/1971 | Mass |
| 3,819,091 A | 6/1974 | Hollender |
| 3,888,258 A | 6/1975 | Akiyama |
| 4,024,859 A | 5/1977 | Slepyan et al. |
| 4,064,873 A | 12/1977 | Swenson |
| 4,073,321 A | 2/1978 | Moskowitz |
| 4,174,716 A | 11/1979 | Treace |
| 4,248,214 A | 2/1981 | Hannah et al. |
| 4,297,749 A | 11/1981 | Davis et al. |
| 4,403,611 A | 9/1983 | Babbitt et al. |
| 4,429,724 A | 2/1984 | Dorros et al. |
| 4,441,216 A | 4/1984 | Ionescu et al. |
| 4,473,073 A | 9/1984 | Darnell |
| D276,937 S | 12/1984 | Griggs |
| 4,535,757 A | 8/1985 | Webster, Jr. |
| 4,546,767 A | 10/1985 | Smith |
| 4,563,178 A | 1/1986 | Santeramo |
| 4,568,337 A | 2/1986 | Treharne, III et al. |
| 4,571,240 A | 2/1986 | Samson |
| 4,608,972 A | 9/1986 | Small |
| 4,637,396 A | 1/1987 | Cook |
| 4,650,488 A | 3/1987 | Bays |
| 4,695,275 A | 9/1987 | Bruce et al. |
| 4,729,763 A | 3/1988 | Henrie |
| 4,737,141 A | 4/1988 | Spits |
| 4,744,366 A | 5/1988 | Jang |
| 4,747,405 A | 5/1988 | Leckrone |
| 4,748,982 A | 6/1988 | Horzewski |
| 4,777,951 A | 10/1988 | Cribier |
| 4,877,030 A | 10/1989 | Beck et al. |
| 4,886,061 A | 12/1989 | Fischell et al. |
| 4,888,017 A | 12/1989 | DeVore et al. |
| 4,898,575 A | 2/1990 | Fischell |
| 4,917,604 A | 4/1990 | Small |
| 4,964,850 A | 10/1990 | Bouton et al. |
| 4,983,167 A | 1/1991 | Sahota |
| 4,994,033 A | 2/1991 | Shockey |
| 5,009,659 A | 4/1991 | Hamlin |
| 5,012,809 A | 5/1991 | Shulze |
| 5,019,042 A | 5/1991 | Sahota |
| 5,026,366 A | 6/1991 | Leckrone |
| 5,026,378 A | 6/1991 | Goldsmith, III |
| 5,030,201 A | 7/1991 | Palestrant |
| 5,032,123 A | 7/1991 | Katz et al. |
| 5,047,040 A | 9/1991 | Simpson |
| 5,049,132 A | 9/1991 | Shaffer et al. |
| 5,053,040 A | 10/1991 | Goldsmith, III |
| 5,057,120 A | 10/1991 | Farcot |
| 5,078,723 A | 1/1992 | Dance |
| 5,080,660 A | 1/1992 | Buelna |
| 5,090,958 A | 2/1992 | Sahota |
| 5,098,381 A | 3/1992 | Schneider |
| 5,112,305 A | 5/1992 | Barath |
| 5,147,377 A | 9/1992 | Sahota |
| 5,160,321 A | 11/1992 | Sahota |
| 5,167,686 A | 12/1992 | Wong |
| 5,176,649 A | 1/1993 | Wakabayashi |
| 5,176,693 A | 1/1993 | Pannek, Jr. |
| 5,181,920 A | 1/1993 | Mueller |
| 5,192,291 A | 3/1993 | Pannek, Jr. |
| 5,196,024 A | 3/1993 | Barath |
| 5,209,749 A | 5/1993 | Buelna |
| 5,213,576 A | 5/1993 | Abiuso |
| 5,224,945 A | 7/1993 | Pannek |
| 5,224,949 A | 7/1993 | Gomringer |
| 5,226,887 A | 7/1993 | Farr |
| 5,232,444 A | 8/1993 | Just |
| 5,232,445 A | 8/1993 | Banzel |
| 5,236,413 A | 8/1993 | Feiring |
| 5,246,455 A | 9/1993 | Shikani |
| 5,261,879 A | 11/1993 | Brill |
| 5,263,952 A | 11/1993 | Grace et al. |
| 5,273,536 A | 12/1993 | Savas |
| 5,295,962 A | 3/1994 | Crocker |
| 5,300,085 A | 4/1994 | Yock |
| 5,304,135 A | 4/1994 | Shonk |
| 5,318,531 A | 6/1994 | Leone |
| 5,320,605 A | 6/1994 | Sahota |
| 5,320,634 A | 6/1994 | Vigil |
| 5,334,147 A | 8/1994 | Johnson |
| 5,336,178 A | 8/1994 | Kaplan |
| 5,336,234 A | 8/1994 | Vigil |
| 5,338,298 A | 8/1994 | McIntyre |
| 5,342,301 A | 8/1994 | Saab |
| 5,342,305 A | 8/1994 | Shonk |
| 5,344,419 A | 9/1994 | Spears |
| 5,372,601 A | 12/1994 | Lary |
| 5,380,304 A | 1/1995 | Parker |
| 5,395,332 A | 3/1995 | Ressemann |
| 5,409,454 A | 4/1995 | Fischell |
| 5,411,478 A | 5/1995 | Stillabower |
| 5,411,552 A | 5/1995 | Andersen et al. |
| 5,431,673 A | 7/1995 | Summers |
| 5,441,510 A | 8/1995 | Simpson |
| 5,447,497 A | 9/1995 | Sogard |
| 5,450,843 A | 9/1995 | Moll |
| 5,456,680 A | 10/1995 | Taylor et al. |
| 5,458,568 A | 10/1995 | Racchini |
| 5,463,280 A | 10/1995 | Johnson |
| 5,466,239 A | 11/1995 | Cinberg |
| 5,496,329 A | 3/1996 | Reisinger |
| 5,496,338 A | 3/1996 | Miyagi et al. |
| 5,505,725 A | 4/1996 | Samson |
| 5,522,790 A | 6/1996 | Moll |
| 5,533,968 A | 7/1996 | Muni |
| 5,536,252 A | 7/1996 | Imran |
| 5,545,215 A | 8/1996 | Duran |
| 5,547,472 A | 8/1996 | Onishi |
| 5,556,408 A | 9/1996 | Farhat |
| 5,558,642 A | 9/1996 | Schweich, Jr. |
| 5,569,184 A | 10/1996 | Crocker |
| 5,569,277 A | 10/1996 | Evans |
| 5,571,087 A | 11/1996 | Ressemann |
| 5,571,089 A | 11/1996 | Crocker |
| 5,575,771 A | 11/1996 | Walinsky |
| 5,601,582 A | 2/1997 | Shelton |
| 5,607,465 A | 3/1997 | Camilli |
| 5,608,628 A | 3/1997 | Keranen |
| 5,609,574 A | 3/1997 | Kaplan |
| 5,611,775 A | 3/1997 | Machold |
| 5,616,149 A | 4/1997 | Barath |
| 5,624,704 A | 4/1997 | Darouiche |
| 5,628,746 A | 5/1997 | Clayman |
| 5,645,562 A | 7/1997 | Haan et al. |
| 5,645,789 A | 7/1997 | Roucher, Jr. |
| 5,649,909 A | 7/1997 | Cornelius |
| 5,649,932 A | 7/1997 | Fouin et al. |
| 5,653,230 A | 8/1997 | Ciaglia et al. |
| 5,669,874 A | 9/1997 | Feiring |
| 5,674,191 A | 10/1997 | Edwards et al. |
| 5,685,847 A | 11/1997 | Barry |
| 5,690,642 A | 11/1997 | Osborne |
| 5,704,913 A | 1/1998 | Abele |
| 5,709,707 A | 1/1998 | Lock et al. |
| 5,713,913 A | 2/1998 | Lary et al. |
| 5,713,953 A | 2/1998 | Vallana et al. |
| 5,720,726 A | 2/1998 | Marcadis |

(56) References Cited

U.S. PATENT DOCUMENTS

| | | |
|---|---|---|
| 5,722,949 A | 3/1998 | Sanese |
| 5,722,979 A | 3/1998 | Kusleika |
| 5,730,733 A | 3/1998 | Mortier |
| 5,733,325 A | 3/1998 | Robinson et al. |
| 5,755,685 A | 5/1998 | Andersen |
| 5,766,203 A | 6/1998 | Imran |
| 5,779,698 A | 7/1998 | Clayman |
| 5,791,341 A | 8/1998 | Bullard |
| 5,792,106 A | 8/1998 | Mische |
| 5,792,158 A | 8/1998 | Lary |
| 5,797,878 A | 8/1998 | Bleam |
| 5,797,935 A | 8/1998 | Barath |
| 5,800,392 A | 9/1998 | Racchini |
| 5,810,867 A | 9/1998 | Zarbatany |
| 5,814,061 A | 9/1998 | Osborne |
| 5,823,996 A | 10/1998 | Sparks |
| 5,824,042 A | 10/1998 | Lombardi et al. |
| 5,840,081 A | 11/1998 | Anderson et al. |
| 5,855,601 A | 1/1999 | Bessler et al. |
| 5,866,561 A | 2/1999 | Ungs |
| 5,879,382 A | 3/1999 | Boneau |
| 5,904,679 A | 5/1999 | Clayman |
| 5,907,893 A | 6/1999 | Zadno-Azizi et al. |
| 5,910,144 A | 6/1999 | Hayashi |
| 5,921,958 A | 7/1999 | Ressemann |
| 5,941,869 A | 8/1999 | Patterson |
| 5,957,949 A | 9/1999 | Leonhardt et al. |
| 5,976,072 A | 11/1999 | Greenberg |
| 5,988,171 A | 11/1999 | Sohn et al. |
| 5,997,570 A | 12/1999 | Ligtenberg |
| 6,010,521 A | 1/2000 | Lee |
| 6,030,405 A | 2/2000 | Zarbatany |
| 6,033,380 A | 3/2000 | Butaric |
| 6,036,654 A | 3/2000 | Quinn |
| 6,036,689 A | 3/2000 | Tu |
| 6,036,708 A | 3/2000 | Sciver |
| 6,048,332 A | 4/2000 | Duffy |
| 6,071,285 A | 6/2000 | Lashinski |
| 6,086,558 A | 7/2000 | Bower et al. |
| 6,099,561 A | 8/2000 | Alt |
| 6,123,718 A | 9/2000 | Tu |
| 6,126,634 A | 10/2000 | Bagaoisan |
| 6,129,706 A | 10/2000 | Janacek |
| 6,129,737 A | 10/2000 | Hamilton |
| 6,143,016 A | 11/2000 | Bleam et al. |
| 6,149,641 A | 11/2000 | Ungs |
| 6,159,179 A | 12/2000 | Simonson |
| 6,159,208 A | 12/2000 | Hovda et al. |
| 6,159,236 A | 12/2000 | Biel |
| 6,161,541 A | 12/2000 | Woodson |
| 6,165,187 A | 12/2000 | Reger |
| 6,206,870 B1 | 3/2001 | Kanner |
| 6,221,043 B1 | 4/2001 | Fischell |
| 6,231,572 B1 | 5/2001 | Hart |
| 6,245,040 B1 | 6/2001 | Inderbitzen |
| 6,254,608 B1 | 7/2001 | Solar |
| 6,258,099 B1 | 7/2001 | Mareiro |
| 6,258,108 B1 | 7/2001 | Lary |
| 6,280,411 B1 | 8/2001 | Lennox |
| 6,280,413 B1 | 8/2001 | Clark et al. |
| 6,280,464 B1 | 8/2001 | Hayashi |
| 6,280,467 B1 | 8/2001 | Leonhardt |
| 6,283,947 B1 | 9/2001 | Mirzaee |
| 6,287,334 B1 | 9/2001 | Moll et al. |
| 6,306,151 B1 | 10/2001 | Lary |
| 6,338,730 B1 | 1/2002 | Bonutti et al. |
| 6,344,028 B1 | 2/2002 | Barry |
| 6,355,013 B1 | 3/2002 | van Muiden |
| 6,371,961 B1 | 4/2002 | Osborne |
| 6,379,323 B1 | 4/2002 | Patterson |
| 6,383,212 B2 | 5/2002 | Durcan |
| 6,397,841 B1 | 6/2002 | Kenyon et al. |
| 6,408,851 B1 | 6/2002 | Karell |
| 6,413,203 B1 | 7/2002 | Sahatjian |
| 6,425,897 B2 | 7/2002 | Overes et al. |
| 6,458,153 B1 | 10/2002 | Bailey et al. |
| 6,488,653 B1 | 12/2002 | Lombardo |
| 6,491,662 B1 | 12/2002 | Liprie |
| 6,494,909 B2 | 12/2002 | Greenhalgh |
| 6,500,186 B2 | 12/2002 | Lafontaine |
| 6,508,824 B1 | 1/2003 | Flaherty |
| 6,513,530 B2 | 2/2003 | Knudson et al. |
| 6,513,531 B2 | 2/2003 | Knudson et al. |
| 6,517,533 B1 | 2/2003 | Swaminathan |
| 6,523,541 B2 | 2/2003 | Knudson et al. |
| 6,540,734 B1 | 4/2003 | Chiu |
| 6,543,452 B1 | 4/2003 | Lavigne |
| 6,544,221 B1 * | 4/2003 | Kokish ................. A61M 25/10 604/103.01 |
| 6,544,223 B1 | 4/2003 | Kokish |
| 6,554,841 B1 | 4/2003 | Yang |
| 6,589,207 B1 | 7/2003 | El-Nounou |
| 6,595,388 B2 | 7/2003 | Mizutani et al. |
| 6,596,021 B1 | 7/2003 | Lootz |
| 6,623,452 B2 | 9/2003 | Chien |
| 6,626,861 B1 | 9/2003 | Hart |
| 6,629,953 B1 | 10/2003 | Boyd |
| 6,632,231 B2 | 10/2003 | Radisch, Jr. |
| 6,659,977 B2 | 12/2003 | Kastenhofer |
| 6,663,590 B2 | 12/2003 | Blatter |
| 6,669,724 B2 | 12/2003 | Park et al. |
| 6,676,698 B2 | 1/2004 | McGuckin, Jr. et al. |
| 6,696,121 B2 | 2/2004 | Jung, Jr. |
| 6,730,105 B2 | 5/2004 | Shiber |
| 6,733,474 B2 | 5/2004 | Kusleika |
| 6,733,486 B1 | 5/2004 | Lee |
| 6,746,463 B1 | 6/2004 | Schwartz |
| 6,747,463 B2 | 6/2004 | Rynhart |
| 6,770,080 B2 | 8/2004 | Kaplan et al. |
| 6,808,518 B2 | 10/2004 | Wellman et al. |
| 6,808,531 B2 | 10/2004 | Lafontaine |
| 6,837,870 B2 | 1/2005 | Duchamp |
| 6,855,124 B1 | 2/2005 | Gonzalez |
| 6,863,856 B1 | 3/2005 | Mahoney |
| 6,878,329 B2 | 4/2005 | Blankenship |
| 6,881,216 B2 | 4/2005 | Di Caprio |
| 6,895,963 B1 | 5/2005 | Martin et al. |
| 6,896,842 B1 | 5/2005 | Hamilton |
| 6,910,483 B2 | 6/2005 | Daly et al. |
| 6,939,320 B2 | 9/2005 | Lennox |
| 6,942,680 B2 | 9/2005 | Grayzel |
| 6,955,172 B2 | 10/2005 | Nelson et al. |
| 6,960,187 B2 | 11/2005 | Kastenhofer |
| 6,966,889 B2 | 11/2005 | Saab |
| 6,974,419 B1 | 12/2005 | Voss et al. |
| 6,989,025 B2 | 1/2006 | Bergmeier |
| 7,004,941 B2 | 2/2006 | Tvinnereim et al. |
| 7,004,963 B2 | 2/2006 | Wang |
| 7,008,438 B2 | 3/2006 | O'Brien |
| 7,037,291 B2 | 5/2006 | Lee |
| 7,044,966 B2 | 5/2006 | Svanidze et al. |
| 7,047,979 B2 | 5/2006 | Conrad et al. |
| 7,048,714 B2 | 5/2006 | Richter |
| 7,063,089 B2 | 6/2006 | Knudson et al. |
| 7,066,905 B2 | 6/2006 | Squire et al. |
| 7,073,505 B2 | 7/2006 | Nelson et al. |
| 7,090,672 B2 | 8/2006 | Underwood et al. |
| 7,101,396 B2 | 9/2006 | Artof et al. |
| 7,115,299 B2 | 10/2006 | Kokish |
| 7,118,551 B1 | 10/2006 | Lee |
| 7,125,404 B2 | 10/2006 | Levatter |
| 7,128,069 B2 | 10/2006 | Farrugia et al. |
| 7,128,759 B2 | 10/2006 | Osborne et al. |
| D534,216 S | 12/2006 | Makower et al. |
| 7,147,661 B2 | 12/2006 | Chobotov et al. |
| 7,168,429 B2 | 1/2007 | Matthews et al. |
| 7,179,251 B2 | 2/2007 | Palasis |
| 7,179,345 B2 | 2/2007 | Shklnik |
| 7,186,237 B2 | 3/2007 | Meyer |
| 7,188,627 B2 | 3/2007 | Nelson et al. |
| 7,195,611 B1 | 3/2007 | Simpson |
| 7,195,641 B2 | 3/2007 | Palmaz et al. |
| 7,213,599 B2 | 5/2007 | Conrad et al. |
| 7,216,647 B2 | 5/2007 | Lang et al. |

(56) References Cited

U.S. PATENT DOCUMENTS

| | | |
|---|---|---|
| 7,225,518 B2 | 6/2007 | Eidenschink |
| 7,235,099 B1 | 6/2007 | Duncavage |
| 7,255,109 B2 | 8/2007 | Knudson et al. |
| 7,269,453 B2 | 9/2007 | Mogul |
| 7,270,673 B2 | 9/2007 | Yee |
| 7,273,471 B1 | 9/2007 | Want et al. |
| 7,279,002 B2 | 10/2007 | Shaw |
| 7,291,112 B2 | 11/2007 | Martin et al. |
| 7,291,158 B2 | 11/2007 | Crow |
| 7,303,572 B2 | 12/2007 | Melsheimer |
| 7,314,364 B2 | 1/2008 | Mahoney |
| 7,329,241 B2 | 2/2008 | Horvath et al. |
| 7,337,778 B2 | 3/2008 | Martin et al. |
| 7,337,781 B2 | 3/2008 | Vassallo |
| 7,338,463 B2 | 3/2008 | Vigil |
| 7,338,471 B2 | 3/2008 | Bates |
| 7,347,869 B2 | 3/2008 | Hojeibane et al. |
| 7,351,238 B2 | 4/2008 | Lee |
| 7,351,256 B2 | 4/2008 | Hojeibane et al. |
| 7,354,419 B2 | 4/2008 | Davies, Jr. |
| 7,354,455 B2 | 4/2008 | Stinson |
| 7,360,542 B2 | 4/2008 | Nelson et al. |
| 7,361,168 B2 | 4/2008 | Makower et al. |
| 7,363,926 B2 | 4/2008 | Pflueger et al. |
| 7,377,938 B2 | 5/2008 | Sarac et al. |
| 7,381,219 B2 | 6/2008 | Salahieh et al. |
| 7,387,634 B2 | 6/2008 | Benderev |
| 7,396,358 B2 | 7/2008 | Appling et al. |
| 7,401,611 B2 | 7/2008 | Conrad et al. |
| 7,410,480 B2 | 8/2008 | Muni et al. |
| 7,413,558 B2 | 8/2008 | Kelley et al. |
| 7,419,497 B2 | 9/2008 | Muni et al. |
| 7,438,925 B2 | 10/2008 | Hsu |
| 7,445,631 B2 | 11/2008 | Salahieh et al. |
| 7,452,371 B2 | 11/2008 | Pavcnik et al. |
| 7,462,175 B2 | 12/2008 | Chang et al. |
| 7,491,188 B2 | 2/2009 | Holman et al. |
| 7,491,200 B2 | 2/2009 | Underwood |
| 7,500,971 B2 | 3/2009 | Chang et al. |
| 7,520,876 B2 | 4/2009 | Ressemann et al. |
| 7,524,331 B2 | 4/2009 | Birdsall |
| 7,544,207 B2 | 6/2009 | Osborne et al. |
| 7,556,642 B2 | 7/2009 | Trotta |
| 7,559,925 B2 | 7/2009 | Goldfarb et al. |
| 7,591,830 B2 | 9/2009 | Rutter |
| 7,607,439 B2 | 10/2009 | Li |
| 7,611,484 B2 | 11/2009 | Wellman et al. |
| 7,625,353 B2 | 12/2009 | Grandt |
| 7,628,769 B2 | 12/2009 | Grandt |
| 7,632,262 B2 | 12/2009 | Bates |
| 7,641,644 B2 | 1/2010 | Chang et al. |
| 7,644,714 B2 | 1/2010 | Atkinson et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,658,192 B2 | 2/2010 | Harrington |
| 7,658,723 B2 | 2/2010 | Von Oepen |
| 7,669,603 B2 | 3/2010 | Knudson et al. |
| 7,673,635 B2 | 3/2010 | Conrad et al. |
| 7,678,099 B2 | 3/2010 | Ressemann et al. |
| 7,680,538 B2 | 3/2010 | Durand et al. |
| 7,703,460 B2 | 4/2010 | Conrad et al. |
| 7,704,259 B2 | 4/2010 | Kaplan et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,740,642 B2 | 6/2010 | Becker |
| 7,744,620 B2 * | 6/2010 | Pedersen ............... A61B 17/22 606/194 |
| 7,753,929 B2 | 7/2010 | Becker |
| 7,753,930 B2 | 7/2010 | Becker |
| 7,771,409 B2 | 8/2010 | Chang et al. |
| 7,785,315 B1 | 8/2010 | Muni et al. |
| 7,789,876 B2 | 9/2010 | Zikorus et al. |
| 7,803,150 B2 | 9/2010 | Chang et al. |
| 7,813,812 B2 | 10/2010 | Kieval et al. |
| 7,827,038 B2 | 11/2010 | Richard et al. |
| 7,827,988 B2 | 11/2010 | Matthews et al. |
| 7,842,062 B2 | 11/2010 | Keith et al. |
| 7,845,357 B2 | 12/2010 | Buscemi et al. |
| 7,854,744 B2 | 12/2010 | Becker |
| 7,856,980 B2 | 12/2010 | Lang et al. |
| 7,862,551 B2 | 1/2011 | Bates |
| 7,874,291 B2 | 1/2011 | Ging et al. |
| 7,879,053 B2 | 2/2011 | Trinidad |
| 7,884,101 B2 | 2/2011 | Teegarden et al. |
| 7,909,037 B2 | 3/2011 | Hegde et al. |
| 7,909,038 B2 | 3/2011 | Hegde et al. |
| 7,921,850 B2 | 4/2011 | Nelson et al. |
| 7,934,506 B2 | 5/2011 | Woodson et al. |
| 7,935,065 B2 | 5/2011 | Martin et al. |
| 7,938,114 B2 | 5/2011 | Matthews et al. |
| 7,949,400 B2 | 5/2011 | Kieval et al. |
| 7,951,130 B2 | 5/2011 | Eaton et al. |
| 7,951,135 B2 | 5/2011 | Eaton et al. |
| 7,954,494 B1 | 6/2011 | Connor |
| 7,955,267 B2 | 6/2011 | Voss et al. |
| 7,959,554 B2 | 6/2011 | McAlexander et al. |
| 7,975,700 B2 | 7/2011 | Frazier et al. |
| 7,976,471 B2 | 7/2011 | Martin et al. |
| 7,976,557 B2 | 7/2011 | Kunis |
| 7,980,248 B2 | 7/2011 | Hegde et al. |
| 7,992,564 B2 | 8/2011 | Doshi et al. |
| 7,992,566 B2 | 8/2011 | Pflueger et al. |
| 7,992,567 B2 | 8/2011 | Hirotsuka et al. |
| 7,993,358 B2 | 8/2011 | O'Brien |
| 7,997,266 B2 | 8/2011 | Frazier et al. |
| 7,997,267 B2 | 8/2011 | Ging et al. |
| 8,020,560 B2 | 9/2011 | Paraschac et al. |
| 8,043,259 B2 | 10/2011 | Radish, Jr. et al. |
| 8,070,693 B2 | 12/2011 | Ayala et al. |
| 8,074,655 B2 | 12/2011 | Sanders |
| 8,096,303 B2 | 1/2012 | Dineen et al. |
| 8,100,933 B2 | 1/2012 | Becker |
| 8,157,857 B2 | 4/2012 | Case et al. |
| 8,167,787 B2 | 5/2012 | Gillis |
| 8,182,446 B2 | 5/2012 | Schaeffer et al. |
| 8,186,355 B2 | 5/2012 | van der Burg et al. |
| 8,192,675 B2 | 6/2012 | Burton et al. |
| 8,211,055 B2 | 7/2012 | Christiansen |
| 8,220,466 B2 | 7/2012 | Frazier et al. |
| 8,220,467 B2 | 7/2012 | Sanders |
| 8,277,478 B2 | 10/2012 | Drontle et al. |
| 8,282,648 B2 | 10/2012 | Tekulve |
| 8,282,667 B2 | 10/2012 | Drontle et al. |
| 8,323,307 B2 | 12/2012 | Hardert |
| 8,327,854 B2 | 12/2012 | Gillis et al. |
| 8,348,890 B2 | 1/2013 | Gerrans |
| 8,435,290 B2 | 5/2013 | Clifford et al. |
| 8,454,637 B2 | 6/2013 | Aggerholm et al. |
| 8,460,322 B2 | 6/2013 | van der Burg et al. |
| 8,535,349 B2 | 9/2013 | Chen et al. |
| 8,540,123 B2 | 9/2013 | Melsheimer et al. |
| 8,603,121 B2 | 12/2013 | Surti et al. |
| 8,740,843 B2 | 6/2014 | Eaton |
| 8,764,705 B2 | 7/2014 | Hennessey |
| 8,771,338 B2 | 7/2014 | Schaeffer et al. |
| 8,808,236 B2 | 8/2014 | Orr |
| 8,911,399 B2 | 12/2014 | Boatman |
| 8,945,142 B2 | 2/2015 | Schaeffer et al. |
| 2001/0018610 A1 | 8/2001 | Limon |
| 2001/0037046 A1 | 11/2001 | Weinberger et al. |
| 2001/0039450 A1 | 11/2001 | Pavcnik et al. |
| 2001/0041859 A1 | 11/2001 | Vigil |
| 2001/0050085 A1 | 12/2001 | Knudson et al. |
| 2001/0051810 A1 | 12/2001 | Dubrul |
| 2002/0010489 A1 | 1/2002 | Grayzel |
| 2002/0032406 A1 | 3/2002 | Kusleika |
| 2002/0042593 A1 | 4/2002 | Mickley |
| 2002/0066450 A1 | 6/2002 | Bonutti |
| 2002/0115982 A1 | 8/2002 | Barbut |
| 2002/0193871 A1 | 12/2002 | Beyersdorf et al. |
| 2003/0028212 A1 | 2/2003 | Saab |

(56) References Cited

U.S. PATENT DOCUMENTS

| | | |
|---|---|---|
| 2003/0032851 A1 | 2/2003 | Apple |
| 2003/0040754 A1 | 2/2003 | Mitchell |
| 2003/0040770 A1 | 2/2003 | Radisch |
| 2003/0047189 A1 | 3/2003 | Kumar et al. |
| 2003/0055444 A1 | 3/2003 | Evans et al. |
| 2003/0055445 A1 | 3/2003 | Evans et al. |
| 2003/0109922 A1 | 6/2003 | Peterson et al. |
| 2003/0111079 A1 | 6/2003 | Matthews et al. |
| 2003/0114868 A1 | 6/2003 | Fischell |
| 2003/0114877 A1 | 6/2003 | Gellman |
| 2003/0114919 A1 | 6/2003 | McQuiston et al. |
| 2003/0130460 A1 | 7/2003 | Freeman et al. |
| 2003/0140925 A1 | 7/2003 | Sapienza et al. |
| 2003/0144677 A1 | 7/2003 | Lary |
| 2003/0153870 A1 | 8/2003 | Meyer |
| 2003/0163148 A1 | 8/2003 | Wang |
| 2003/0168064 A1 | 9/2003 | Daly et al. |
| 2003/0229370 A1 | 12/2003 | Miller |
| 2003/0236568 A1 | 12/2003 | Hojeibane et al. |
| 2004/0019374 A1 | 1/2004 | Hojeibane et al. |
| 2004/0028676 A1 | 2/2004 | Klein et al. |
| 2004/0054351 A1 | 3/2004 | Deniega |
| 2004/0064093 A1 | 4/2004 | Hektner |
| 2004/0064150 A1 | 4/2004 | Becker |
| 2004/0068299 A1 | 4/2004 | Laske et al. |
| 2004/0073297 A1 | 4/2004 | Rohde |
| 2004/0093070 A1 | 5/2004 | Hojeibane et al. |
| 2004/0111108 A1 | 6/2004 | Farnan |
| 2004/0112387 A1 | 6/2004 | Lang et al. |
| 2004/0122457 A1 | 6/2004 | Weber |
| 2004/0122465 A1 | 6/2004 | McMurtry |
| 2004/0127920 A1 | 7/2004 | Radisch |
| 2004/0133223 A1 | 7/2004 | Weber |
| 2004/0143287 A1 | 7/2004 | Konstantino |
| 2004/0153127 A1 | 8/2004 | Gordon et al. |
| 2004/0172121 A1 | 9/2004 | Eidenschinck |
| 2004/0181252 A1 | 9/2004 | Boyle |
| 2004/0187870 A1 | 9/2004 | Matthews et al. |
| 2004/0193196 A1 | 9/2004 | Appling |
| 2004/0199191 A1 | 10/2004 | Schwartz |
| 2004/0230178 A1 | 11/2004 | Wu |
| 2004/0243156 A1 | 12/2004 | Wu |
| 2004/0243158 A1 | 12/2004 | Konstantino |
| 2004/0254538 A1 | 12/2004 | Murphy et al. |
| 2004/0260239 A1 | 12/2004 | Kusleika |
| 2004/0260389 A1 | 12/2004 | Case et al. |
| 2005/0005937 A1 | 1/2005 | Farrugia et al. |
| 2005/0021070 A1 | 1/2005 | Feld |
| 2005/0021071 A1 | 1/2005 | Konstantino |
| 2005/0027246 A1 | 2/2005 | Dion |
| 2005/0033334 A1 | 2/2005 | Santra |
| 2005/0038383 A1 | 2/2005 | Kelley |
| 2005/0059923 A1 | 3/2005 | Gamboa |
| 2005/0075713 A1 | 4/2005 | Biancucci et al. |
| 2005/0080478 A1 | 4/2005 | Barongan |
| 2005/0090845 A1 | 4/2005 | Boyd |
| 2005/0090846 A1 | 4/2005 | Pedersen |
| 2005/0096735 A1 | 5/2005 | Hojeibane et al. |
| 2005/0098184 A1 | 5/2005 | Conrad et al. |
| 2005/0102020 A1 | 5/2005 | Grayzel et al. |
| 2005/0103339 A1 | 5/2005 | Daly et al. |
| 2005/0126563 A1 | 6/2005 | van der Burg et al. |
| 2005/0143817 A1 | 6/2005 | Hunter |
| 2005/0178384 A1 | 8/2005 | Martin et al. |
| 2005/0217673 A1 | 10/2005 | Daly et al. |
| 2005/0240148 A1 | 10/2005 | Cheves |
| 2005/0245906 A1 | 11/2005 | Makower et al. |
| 2005/0267547 A1 | 12/2005 | Knudson et al. |
| 2005/0279365 A1 | 12/2005 | Armijo et al. |
| 2005/0288629 A1 | 12/2005 | Kunis |
| 2005/0288632 A1 | 12/2005 | William |
| 2006/0000475 A1 | 1/2006 | Matthews et al. |
| 2006/0004286 A1 | 1/2006 | Chang et al. |
| 2006/0015133 A1 | 1/2006 | Grayzel |
| 2006/0015134 A1 | 1/2006 | Trinidad |
| 2006/0020256 A1 | 1/2006 | Bell |
| 2006/0063973 A1 | 3/2006 | Makower et al. |
| 2006/0070626 A1 | 4/2006 | Frazier et al. |
| 2006/0095066 A1 | 5/2006 | Chang et al. |
| 2006/0106361 A1 | 5/2006 | Muni et al. |
| 2006/0111736 A1 | 5/2006 | Kelley |
| 2006/0129178 A1 | 6/2006 | Reifart |
| 2006/0149192 A1 | 7/2006 | Deniega |
| 2006/0149308 A1 | 7/2006 | Melsheimer et al. |
| 2006/0150986 A1 | 7/2006 | Roue et al. |
| 2006/0155304 A1 | 7/2006 | Kaplan et al. |
| 2006/0173487 A1 | 8/2006 | Uflacker |
| 2006/0178621 A1 | 8/2006 | Constantz et al. |
| 2006/0178685 A1 | 8/2006 | Melsheimer |
| 2006/0200110 A1 | 9/2006 | Lentz |
| 2006/0207612 A1 | 9/2006 | Jackson et al. |
| 2006/0210605 A1 | 9/2006 | Chang et al. |
| 2006/0224115 A1 | 10/2006 | William |
| 2006/0235877 A1 | 10/2006 | Richard et al. |
| 2006/0258987 A1 | 11/2006 | Lentz |
| 2006/0259005 A1 | 11/2006 | Konstantino et al. |
| 2006/0287665 A1 | 12/2006 | Burton |
| 2007/0038291 A1 | 2/2007 | Case et al. |
| 2007/0066961 A1 | 3/2007 | Rutter |
| 2007/0073329 A1 | 3/2007 | Hardert |
| 2007/0106215 A1 | 5/2007 | Olsen |
| 2007/0112370 A1 | 5/2007 | Andrews |
| 2007/0118076 A1 | 5/2007 | Lim |
| 2007/0129705 A1 | 6/2007 | Trombley et al. |
| 2007/0129751 A1 | 6/2007 | Muni et al. |
| 2007/0132117 A1 | 6/2007 | Truitt et al. |
| 2007/0134085 A1 | 6/2007 | Daly et al. |
| 2007/0135789 A1 | 6/2007 | Chang et al. |
| 2007/0135830 A1 | 6/2007 | Schaeffer |
| 2007/0142771 A1 | 6/2007 | Durcan |
| 2007/0144539 A1 | 6/2007 | van der Burg et al. |
| 2007/0157928 A1 | 7/2007 | Pujol et al. |
| 2007/0157934 A1 | 7/2007 | Lang et al. |
| 2007/0167682 A1 | 7/2007 | Goldfarb et al. |
| 2007/0191781 A1 | 8/2007 | Richards et al. |
| 2007/0207994 A1 | 9/2007 | Teegarden et al. |
| 2007/0208252 A1 | 9/2007 | Makower |
| 2007/0208301 A1 | 9/2007 | Evard et al. |
| 2007/0209664 A1 | 9/2007 | Paraschac et al. |
| 2007/0209665 A1 | 9/2007 | Gillis et al. |
| 2007/0244086 A1 | 10/2007 | Teegarden et al. |
| 2007/0250105 A1 | 10/2007 | Ressemann et al. |
| 2007/0256693 A1 | 11/2007 | Paraschac et al. |
| 2007/0260327 A1 | 11/2007 | Case et al. |
| 2007/0282305 A1 | 12/2007 | Goldfarb et al. |
| 2007/0287923 A1 | 12/2007 | Adkins et al. |
| 2007/0293727 A1 | 12/2007 | Goldfarb et al. |
| 2008/0015472 A1 | 1/2008 | Ressemann et al. |
| 2008/0015497 A1 | 1/2008 | Keith et al. |
| 2008/0015540 A1 | 1/2008 | Muni et al. |
| 2008/0015544 A1 | 1/2008 | Keith et al. |
| 2008/0015626 A1 | 1/2008 | Keith et al. |
| 2008/0023012 A1 | 1/2008 | Dineen et al. |
| 2008/0027560 A1 | 1/2008 | Jackson et al. |
| 2008/0033353 A1 | 2/2008 | Truitt et al. |
| 2008/0036368 A1 | 2/2008 | Frampton et al. |
| 2008/0041382 A1 | 2/2008 | Matthews et al. |
| 2008/0041383 A1 | 2/2008 | Matthews et al. |
| 2008/0045813 A1 | 2/2008 | Phuah et al. |
| 2008/0053461 A1 | 3/2008 | Hirotsuka et al. |
| 2008/0058584 A1 | 3/2008 | Hirotsuka et al. |
| 2008/0066753 A1 | 3/2008 | Martin et al. |
| 2008/0066765 A1 | 3/2008 | Paraschac et al. |
| 2008/0066769 A1 | 3/2008 | Dineen et al. |
| 2008/0077164 A1 | 3/2008 | Murphy |
| 2008/0077165 A1 | 3/2008 | Murphy |
| 2008/0091067 A1 | 4/2008 | Dollar |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097380 A1 | 4/2008 | Li |
| 2008/0097400 A1 | 4/2008 | Chang et al. |
| 2008/0097514 A1 | 4/2008 | Chang et al. |
| 2008/0097515 A1 | 4/2008 | Chang et al. |

(56) References Cited

U.S. PATENT DOCUMENTS

| | | |
|---|---|---|
| 2008/0097516 A1 | 4/2008 | Chang et al. |
| 2008/0099019 A1 | 5/2008 | Martin et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0154237 A1 | 6/2008 | Chang et al. |
| 2008/0154250 A1 | 6/2008 | Makower et al. |
| 2008/0157444 A1 | 7/2008 | Melsheimer |
| 2008/0171991 A1 | 7/2008 | Kourakis |
| 2008/0172033 A1 | 7/2008 | Keith et al. |
| 2008/0194953 A1 | 8/2008 | Kerber |
| 2008/0195041 A1 | 8/2008 | Goldfarb et al. |
| 2008/0208265 A1 | 8/2008 | Frazier et al. |
| 2008/0228085 A1 | 9/2008 | Jenkins et al. |
| 2008/0228139 A1 | 9/2008 | Melsheimer et al. |
| 2008/0234720 A1 | 9/2008 | Chang et al. |
| 2008/0243140 A1 | 10/2008 | Gopferich et al. |
| 2008/0249500 A1 | 10/2008 | Keith et al. |
| 2008/0251071 A1 | 10/2008 | Armitstead et al. |
| 2008/0255507 A1 | 10/2008 | Mushtaha |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0275483 A1 | 11/2008 | Makower et al. |
| 2008/0281156 A1 | 11/2008 | Makower et al. |
| 2008/0281300 A1 | 11/2008 | Morriss |
| 2008/0287908 A1 | 11/2008 | Muni et al. |
| 2008/0300610 A1 | 12/2008 | Chambers |
| 2008/0319424 A1 | 12/2008 | Muni et al. |
| 2009/0005754 A1 | 1/2009 | Soetermans |
| 2009/0005763 A1 | 1/2009 | Makower et al. |
| 2009/0018501 A1 | 1/2009 | Yribarren |
| 2009/0018502 A1 | 1/2009 | Reifart |
| 2009/0028923 A1 | 1/2009 | Muni et al. |
| 2009/0030274 A1 | 1/2009 | Goldfarb et al. |
| 2009/0043263 A1 | 2/2009 | Woodard, Jr. et al. |
| 2009/0044814 A1 | 2/2009 | Iancea et al. |
| 2009/0053306 A1 | 2/2009 | Agarwal et al. |
| 2009/0060905 A1 | 3/2009 | Martin et al. |
| 2009/0076439 A1 | 3/2009 | Dollar et al. |
| 2009/0076446 A1 | 3/2009 | Dubuclet, IV et al. |
| 2009/0088599 A1 | 4/2009 | Zook et al. |
| 2009/0088728 A1 | 4/2009 | Dollar et al. |
| 2009/0093823 A1 | 4/2009 | Chang et al. |
| 2009/0099471 A1 | 4/2009 | Broadley et al. |
| 2009/0131923 A1 | 5/2009 | Connors et al. |
| 2009/0163848 A1 | 6/2009 | Morriss et al. |
| 2009/0163890 A1 | 6/2009 | Clifford et al. |
| 2009/0171283 A1 | 7/2009 | Schaeffer et al. |
| 2009/0171336 A1 | 7/2009 | Weber |
| 2009/0187098 A1 | 7/2009 | Makower et al. |
| 2009/0192537 A1 | 7/2009 | O'Brien |
| 2009/0198216 A1 | 8/2009 | Muni et al. |
| 2009/0216196 A1 | 8/2009 | Drontle et al. |
| 2009/0221988 A1 | 9/2009 | Ressemann et al. |
| 2009/0234283 A1 | 9/2009 | Burton et al. |
| 2009/0240112 A1 | 9/2009 | Goldfarb et al. |
| 2009/0240237 A1 | 9/2009 | Goldfarb et al. |
| 2009/0254064 A1 | 10/2009 | Boatman |
| 2009/0270815 A1 | 10/2009 | Stamp et al. |
| 2009/0299327 A1 | 12/2009 | Tilson et al. |
| 2009/0299374 A1 | 12/2009 | Tilson et al. |
| 2009/0299379 A1 | 12/2009 | Katz et al. |
| 2009/0299401 A1 | 12/2009 | Tilson et al. |
| 2009/0306582 A1 | 12/2009 | Granada et al. |
| 2009/0306589 A1 | 12/2009 | Tilson et al. |
| 2009/0312745 A1 | 12/2009 | Goldfarb et al. |
| 2009/0312807 A1 | 12/2009 | Boudreault et al. |
| 2010/0004264 A1 | 1/2010 | Xiang et al. |
| 2010/0010061 A1 | 1/2010 | Cooper et al. |
| 2010/0010470 A1 | 1/2010 | Bates |
| 2010/0016694 A1 | 1/2010 | Martin et al. |
| 2010/0028026 A1 | 2/2010 | Inami et al. |
| 2010/0030031 A1 | 2/2010 | Goldfarb et al. |
| 2010/0030113 A1 | 2/2010 | Morriss et al. |
| 2010/0042046 A1 | 2/2010 | Chang et al. |
| 2010/0049166 A1 | 2/2010 | Koenig et al. |
| 2010/0069900 A1 | 3/2010 | Shirley |
| 2010/0076269 A1 | 3/2010 | Makower et al. |
| 2010/0076437 A1 | 3/2010 | Tilson et al. |
| 2010/0094137 A1 | 4/2010 | Furlong et al. |
| 2010/0094259 A1 | 4/2010 | Makower et al. |
| 2010/0099946 A1 | 4/2010 | Jenkins et al. |
| 2010/0100181 A1 | 4/2010 | Makower et al. |
| 2010/0106246 A1 | 4/2010 | Rousseau et al. |
| 2010/0108066 A1 | 5/2010 | Martin et al. |
| 2010/0108077 A1 | 5/2010 | Lindh et al. |
| 2010/0114066 A1 | 5/2010 | Makower et al. |
| 2010/0121308 A1 | 5/2010 | Muni et al. |
| 2010/0132719 A1 | 6/2010 | Jacobs et al. |
| 2010/0144701 A1 | 6/2010 | Cooper et al. |
| 2010/0152654 A1 | 6/2010 | Tilson et al. |
| 2010/0168511 A1 | 7/2010 | Muni et al. |
| 2010/0174138 A1 | 7/2010 | Chang et al. |
| 2010/0174308 A1 | 7/2010 | Chang et al. |
| 2010/0185146 A1 | 7/2010 | Ramzipoor |
| 2010/0198135 A1 | 8/2010 | Morriss et al. |
| 2010/0198191 A1 | 8/2010 | Clifford et al. |
| 2010/0198247 A1 | 8/2010 | Chang et al. |
| 2010/0210901 A1 | 8/2010 | Makower et al. |
| 2010/0211007 A1 | 8/2010 | Lesch, Jr. et al. |
| 2010/0217296 A1 | 8/2010 | Morriss et al. |
| 2010/0234946 A1 | 9/2010 | Rousseau |
| 2010/0241152 A1 | 9/2010 | Tilson et al. |
| 2010/0241153 A1 | 9/2010 | Tilson et al. |
| 2010/0241155 A1 | 9/2010 | Chang et al. |
| 2010/0241178 A1 | 9/2010 | Tilson et al. |
| 2010/0256653 A1 | 10/2010 | Kaplan et al. |
| 2010/0268245 A1 | 10/2010 | Chang et al. |
| 2010/0274188 A1 | 10/2010 | Chang et al. |
| 2010/0274222 A1 | 10/2010 | Setliff, III et al. |
| 2010/0274271 A1 | 10/2010 | Kelley |
| 2010/0282774 A1 | 11/2010 | Greter et al. |
| 2010/0298862 A1 | 11/2010 | Chang et al. |
| 2010/0300458 A1 | 12/2010 | Stubbs et al. |
| 2011/0004057 A1 | 1/2011 | Goldfarb et al. |
| 2011/0015612 A1 | 1/2011 | Arcand et al. |
| 2011/0046654 A1 | 2/2011 | Kuppurathanam |
| 2011/0056498 A1 | 3/2011 | Lang et al. |
| 2011/0060276 A1 | 3/2011 | Schaeffer et al. |
| 2011/0071349 A1 | 3/2011 | Drontle et al. |
| 2011/0094520 A1 | 4/2011 | Mikhailenok et al. |
| 2011/0060214 A1 | 5/2011 | Makower |
| 2011/0100376 A1 | 5/2011 | Rousseau |
| 2011/0100378 A1 | 5/2011 | Rousseau |
| 2011/0112512 A1 | 5/2011 | Muni et al. |
| 2011/0130249 A1 | 6/2011 | Mikhailenok et al. |
| 2011/0137245 A1 | 6/2011 | Schaeffer |
| 2011/0160575 A1 | 6/2011 | Beyar et al. |
| 2011/0160740 A1 | 6/2011 | Makower et al. |
| 2011/0166673 A1 | 7/2011 | Patel et al. |
| 2011/0183928 A1 | 7/2011 | Thede et al. |
| 2011/0201996 A1 | 8/2011 | Melder |
| 2011/0202037 A1 | 8/2011 | Bolger |
| 2011/0224652 A1 | 9/2011 | Drontle et al. |
| 2011/0226264 A1 | 9/2011 | Friedman |
| 2011/0245850 A1 | 10/2011 | van der Burg et al. |
| 2011/0288477 A1 | 11/2011 | Ressemann et al. |
| 2011/0295237 A1 | 12/2011 | Eells et al. |
| 2011/0308530 A1 | 12/2011 | Gillis et al. |
| 2011/0313355 A1 | 12/2011 | Boatman |
| 2011/0313400 A1 | 12/2011 | Boatman |
| 2011/0319976 A1 | 12/2011 | Iyer et al. |
| 2012/0010646 A1 | 1/2012 | Keith et al. |
| 2012/0016298 A1 | 1/2012 | DeLegge |
| 2012/0071824 A1 | 3/2012 | Chang et al. |
| 2012/0116254 A1 | 5/2012 | Morriss |
| 2012/0136207 A1 | 5/2012 | Goldfarb et al. |
| 2012/0143054 A1 | 6/2012 | Eaton |

(56) References Cited

U.S. PATENT DOCUMENTS

| | | |
|---|---|---|
| 2012/0172912 A1 | 7/2012 | Ressemann et al. |
| 2012/0184983 A1 | 7/2012 | Chang et al. |
| 2012/0190973 A1 | 7/2012 | Ressemann et al. |
| 2012/0195157 A1 | 8/2012 | McKay |
| 2012/0226230 A1 | 9/2012 | Gerrans |
| 2012/0245419 A1 | 9/2012 | Makower et al. |
| 2012/0245590 A1 | 9/2012 | Melsheimer et al. |
| 2012/0265094 A1 | 10/2012 | Goldfarb et al. |
| 2012/0283625 A1 | 11/2012 | Keith et al. |
| 2012/0303011 A1 | 11/2012 | Schaeffer |
| 2012/0310210 A1 | 12/2012 | Campbell et al. |
| 2012/0316436 A1 | 12/2012 | Lentz et al. |
| 2013/0056009 A1 | 3/2013 | Mohan et al. |
| 2013/0060267 A1 | 3/2013 | Farnan et al. |
| 2013/0085546 A1 | 4/2013 | Bolea et al. |
| 2013/0096605 A1 | 4/2013 | Becker |
| 2013/0158559 A1 | 6/2013 | Schaeffer |
| 2013/0178790 A1 | 7/2013 | Tekulve |
| 2013/0180528 A1 | 7/2013 | Zhou et al. |
| 2013/0213409 A1 | 8/2013 | Podmore et al. |
| 2013/0245662 A1 | 9/2013 | Schaeffer et al. |
| 2013/0261655 A1 | 10/2013 | Drasler et al. |
| 2013/0289706 A1 | 10/2013 | Schaeffer et al. |
| 2014/0031792 A1 | 1/2014 | Schaeffer et al. |
| 2014/0088624 A1 | 3/2014 | Burton et al. |
| 2014/0100592 A1 | 4/2014 | Burton et al. |
| 2014/0155927 A1 | 6/2014 | Burton |
| 2014/0379070 A1 | 12/2014 | Schaeffer et al. |

FOREIGN PATENT DOCUMENTS

| | | |
|---|---|---|
| EP | 0577400 | 1/1994 |
| EP | 0835673 A2 | 4/1998 |
| EP | 0850607 | 7/1998 |
| EP | 083567 A3 | 9/1999 |
| EP | 1159924 | 12/2001 |
| EP | 1230944 | 8/2002 |
| EP | 2478929 | 7/2012 |
| EP | 2522386 | 11/2012 |
| JP | 62-227352 | 8/1994 |
| WO | 8302225 | 7/1983 |
| WO | WO9619257 | 6/1996 |
| WO | WO9734649 | 9/1997 |
| WO | 0154625 | 8/2001 |
| WO | WO0160443 | 8/2001 |
| WO | 03030776 | 4/2003 |
| WO | WO03047468 | 6/2003 |
| WO | WO2003063711 | 8/2003 |
| WO | WO2004060460 | 7/2004 |
| WO | WO2006020180 | 2/2006 |
| WO | WO2006074256 | 7/2006 |
| WO | WO2006114783 | 11/2006 |
| WO | WO2006119512 | 11/2006 |
| WO | WO2006136964 | 12/2006 |
| WO | WO2007065137 | 6/2007 |
| WO | WO2007149469 | 12/2007 |
| WO | WO2008036368 | 3/2008 |
| WO | WO2008045242 | 4/2008 |
| WO | WO2009033026 | 3/2009 |
| WO | WO2009036118 | 3/2009 |
| WO | WO2009114425 | 9/2009 |
| WO | WO2009140197 | 11/2009 |
| WO | WO2010022108 | 2/2010 |
| WO | WO2009036135 | 3/2010 |
| WO | WO2010024871 | 3/2010 |
| WO | WO2010025299 | 3/2010 |
| WO | WO2010045546 | 4/2010 |
| WO | WO2010051195 | 5/2010 |
| WO | WO2010065030 | 6/2010 |
| WO | WO2010120620 | 10/2010 |
| WO | WO2011068952 | 6/2011 |
| WO | WO2011082074 | 7/2011 |
| WO | WO2011084655 | 7/2011 |
| WO | 2011123714 | 10/2011 |
| WO | WO2012037162 | 3/2012 |
| WO | WO2012156914 | 11/2012 |
| WO | WO2012170860 | 12/2012 |
| WO | WO2013010169 | 1/2013 |
| WO | WO2014070966 | 5/2014 |
| WO | WO2014189540 | 11/2014 |

OTHER PUBLICATIONS

Woodson et al. Response to: Multicenter study of a novel adjustable tongue-advacement device for obstructive sleep apnea [article]. Otolaryngology—head and neck surgery, vol. 144, No. 6, pp. 1009-1012. 2011. SAGE.

Siesta Medical. Siesta Medical receives 510(k) clearance for Encore system to treat obstructive sleep apnea [press release]. Sep. 12, 2011. pp. 1-2.

Aspire Medical, Inc. Aspire Medical announces first implant in US and start of clinical trial to treat sleep apnea [article]. Medical News Today. May 23, 2007. pp. 1-4. URL: <http://www.medicalnewstoday.com/releases/71787.php>.

Hamans et al. A novel tongue implant for tongue advancement for obstructive sleep apnea: feasibility, safety and histology in a canine model [article]. J Musculoskelet Neuronal Interact. vol. 10, No. 1, pp. 100-111. Dec. 29, 2009. Hylonome.

Knobbe, Martens, Olson & Bear, LLP. Amendment and response to non-Final Office Action dated Jan. 18, 2013, for U.S. Appl. No. 13/077,813, filed Mar. 31, 2011. First Named Inventor, van der Burg. Title, Suture Passer Systems and Methods for Tongue or Other Tissue Suspension and Compression.

PR Newswire. Aspire Medical appoints Roseanne Varner as president and CEO [press release]. pp. 1-2. May 1, 2011. URL: <http://www.prnewswire.com/news-releases/aspire-medical-appoints-roseanne-varner-as-president-and-ceo-57760852.html>.

Park. Aspire Medical Advance System for obstructive sleep apnea [blog]. Dr. Park: Breathe better, sleep better, live better. pp. 1-4. Oct. 6, 2010. URL: <http://doctorstevenpark.com/aspire-medical-advance-system-for-obstructive-sleep-apnea>.

Revent Medical. The Revent Solution: Tongue Implanter Kit [webpage]. 2014. pp. 1-2. Retrieved Aug. 12, 2014. URL: <http://www.reventmedical.com/solution/>.

Revent Medical. The Revent Solution: Implants [webpage]. 2014. pp. 1-2. Retrieved Aug. 12, 2014. URL: <www.reventmedical.com/solution/>.

European Patent Office, "Extended European Search Report," for application No. 15152386.7, dated Jun. 18, 2015, pp. 1-5.

Geisthoff, Urban W., Basic Sialendoscopy Techniques, Otolaryngol Clin N Am, 2009, p. 1029-1052, vol. 42, Elsevier Inc.

European Patent Office, Extended European Search Report, Patent App. No. 13178419.1, dated Nov. 27, 2013, pp. 2-8.

Dorado PTA Dilation Catheter Brochure, Bard Peripheral Vascular, 2011, 4 pgs.

ATOS Medical, SinoJect brochure, 2012.

International Searching Authority, International Search Report and the Written Opinion, for International Application No. PCT/US2012/046923, dated Nov. 2, 2012, p. 1-18.

File history of U.S. Appl. No. 08/883,220, now U.S. Pat. No. 5,988,171, as of Nov. 21, 2013. filed Jun. 26, 1997. First Named Inventor, Ze'ev Sohn. Title, Methods and Devices for the Treatment of Airway Obstruction, Sleep Apnea and Snoring.

File history of U.S. Appl. No. 10/877,003, now U.S. Pat. No. 7,213,599, as of Nov. 21, 2013. filed Jun. 24, 2004. First Named Inventor, Timothy R. Conrad. Title, Airway Implant.

File history of U.S. Appl. No. 11/757,501, now U.S. Pat. No. 7,703,460, as of Nov. 21, 2013. filed Jun. 4, 2007. First Named Inventor, Timothy R. Conrad. Title, Tongue Implant.

File history of U.S. Appl. No. 12/214,084 as of Nov. 21, 2013. filed Jun. 17, 2008. First Named Inventor, Octavian Iancea. Title, Implantable devices, systems, and methods of maintaining desired orientations in targeted tissue regions.

International Searching Authority, International Preliminary Report on Patentability, for International Application No. PCT/US2012/046923, dated Jan. 23, 2014, p. 1-7.

(56) References Cited

OTHER PUBLICATIONS

Katsanos, et al., Paclitaxel-coated balloon angioplasty vs. plain balloon dilation for the treatment of failing dialysis access: 6-month interim results from a prospective randomized controlled trial, J. Endovasc. Ther., Apr. 2012; 19(2): pp. 263-272.
Roy-Chaudhury, et al., Biology of arteriovenous fistula failure, J. Nephrol. Mar.-Apr. 2007; 20(2); pp. 150-163.
Krokidis, Peripheral Applications of Drug-Coated Balloons: Past, Present and Future; CardioVascular and Interventional Radiology, Apr. 2013, vol. 36, Issue 2, pp. 281-291.
European Patent Office, International Preliminary Report on Patentability, App. No. PCT/US2012/041622, dated Dec. 27, 2013, pp. 2-11.
Panjehpour, Masoud and Bergein F. Overholt, Photodynamic Therapy for Barrett's Esophagus, Interventional and Therapeutic Gastrointestinal Endoscopy (Frontiers of Gastrointestinal Research), 2010, vol. 27, pp. 128-129, S. Karger AG, Basel (Switzerland).
ClearWay OTW Local Therapeutic Infusion Catheter. Product information [online], Atrium. Retrieved from the internet: URL: http://www.atriumnned.com/EN/Interventional/clearway.asp.
ClearWay RX Local Therapeutic Infusion Catheter. Product information [online], Atrium. Retrieved from the internet: URL: http://www.atriumnried.com/EN/cardiology/clearway.asp.
Relieva Stratus MicroFlow Spacers & Relieva Stratus Deployment Guides. Intructions for Use, Acclarent Inc., pp. 1-8.
Relieva Ultirra Sinus Balloon Catheter. Intructions for Use, Acclarent Inc., pp. 1-11.
Flextome Cutting Balloon Dilatation Device. Product Information [online], Boston Scientific [retrieved Feb. 10, 2015]. Retrieved from the internet: URL: http://www.bostonscientific.com/en-US/products/plaque-modification/flextome-cutting-balloon-dilatation-device.html.
XprESS Multi-Sinus Dilation Tool. Instructions for Use, Entellus Medical, May 2011, pp. 1-6.
XprESS Multi-Sinus Dilation Tool Using Bending Tool. Instructions for Use, Entellus Medical, Sep. 2011, pp. 1-7.
International Search Report for International Application No. PCT/US2009/054236, dated Apr. 16, 2010, p. 1-4.
Written Opinion of the International Searching Authority for International Application No. PCT/U52009/054236, dated Apr. 16, 2010, p. 1-4.
International Preliminary Report on Patentability for International Application No. PCT/US2009/054236, dated Feb. 22, 2011.
International Search Report for International Application No. PCT/US2009/055252, dated Apr. 20, 2010, p. 1-4.
Written Opinion of the International Searching Authority for International Application No. PCT/US2009/055252, dated Apr. 20, 2010, p. 1-4.
International Preliminary Report on Patentability for International Application No. PCT/US2009/055252, dated Mar. 1, 2011, p. 1-5.
IP Australia, "Patent Examination Report No. 2," for Application No. 2011253707, dated May 13, 2014, pp. 1-6.
Taghi, A.S. et al., "Balloon Sinuplasty: balloon-catheter dilation of paranasal sinus ostia for chronic rhinosinusitis," Expert Reviews Medical Devices, 2009, vol. 6(4), pp. 377-382.
Bolger W.E., et al., "Safety and outcomes of balloon catheter sinusotomy: A multicenter 24-week analysis in 115 patients," Otolaryngology-Head and Neck Surgery, 2007, vol. 137, pp. 10-20.
Kuhn F.A. et al., "Balloon catheter sinusotomy: One-year follow-up—Outcomes and role in functional endoscopic sinus surgery," Otolaryngology-Head and Neck Surgery, 2008, vol. 139, S27-S37.
International Searching Authority, International Search Report and Written Opinion for International application No. PCT/US2014/049341, dated Nov. 19, 2014, pp. 1-11.
Ngu, RK, et al., "Salivary duct strictures: nature and incidence in benign salivary obstruction," Dentomaxillofacial Radiology, 2007 vol. 36, pp. 63-67.
Briffa, N.P., et al., "Use of an embolectomy catheter to remove a submandibular duct stone," British Journal of Surgery, 1989 vol. 76, p. 814.
Guest P., et al., "Non-operative removal of a parotid duct stone with a balloon angioplasty catheter," British Journal of Oral and Maxillofacial Surgery, 1992.
European Search Report and Search Opinion, issued by the European Patent Office, dated Nov. 9, 2009 for Application No. 09170581.4-2320.
U.S. Appl. No. 12/614,878, Final Office Action dated Dec. 27, 2010.

\* cited by examiner

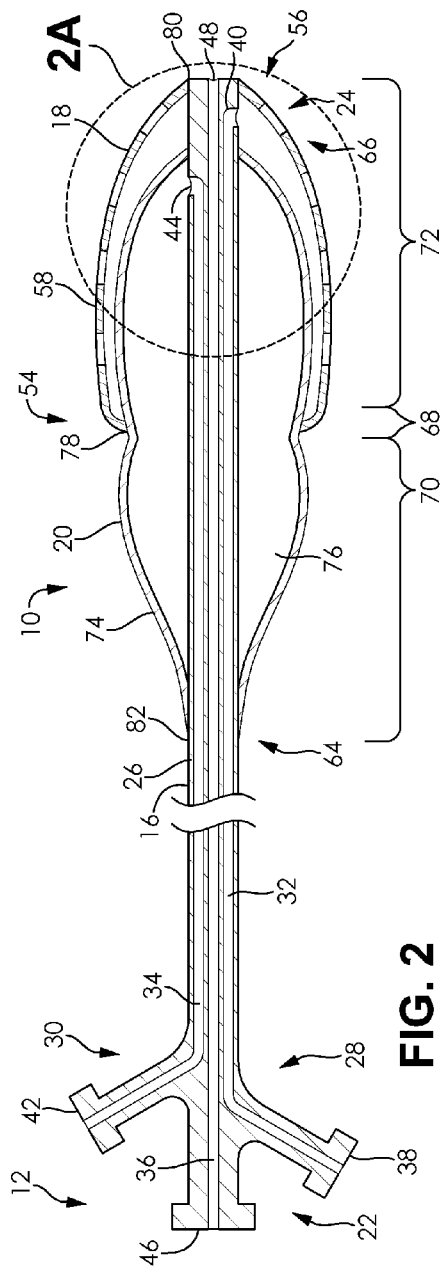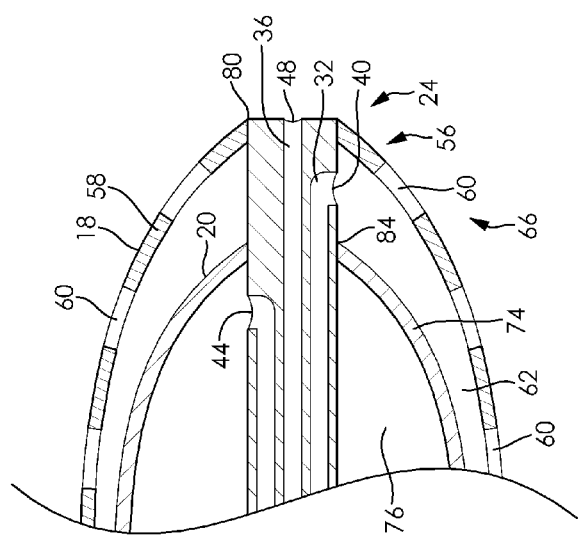

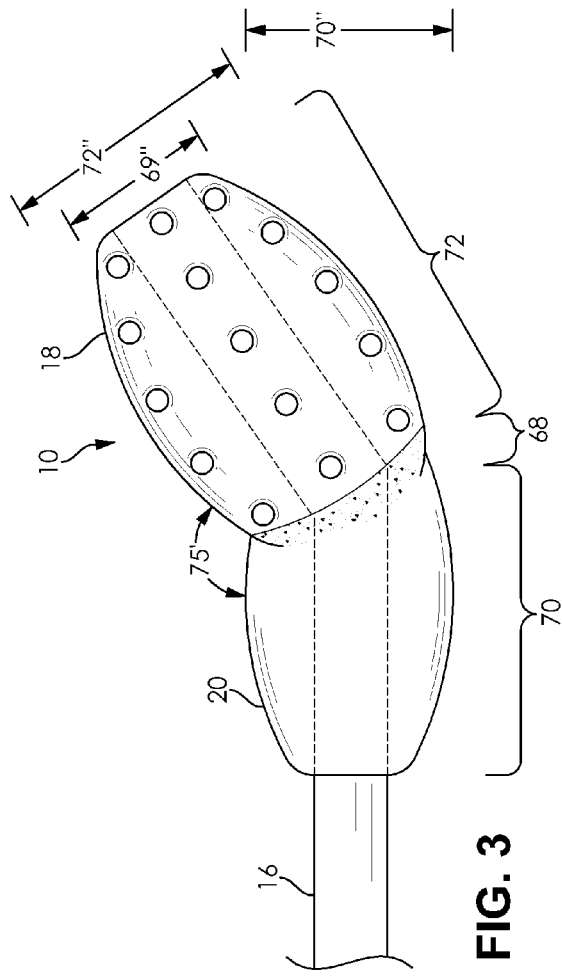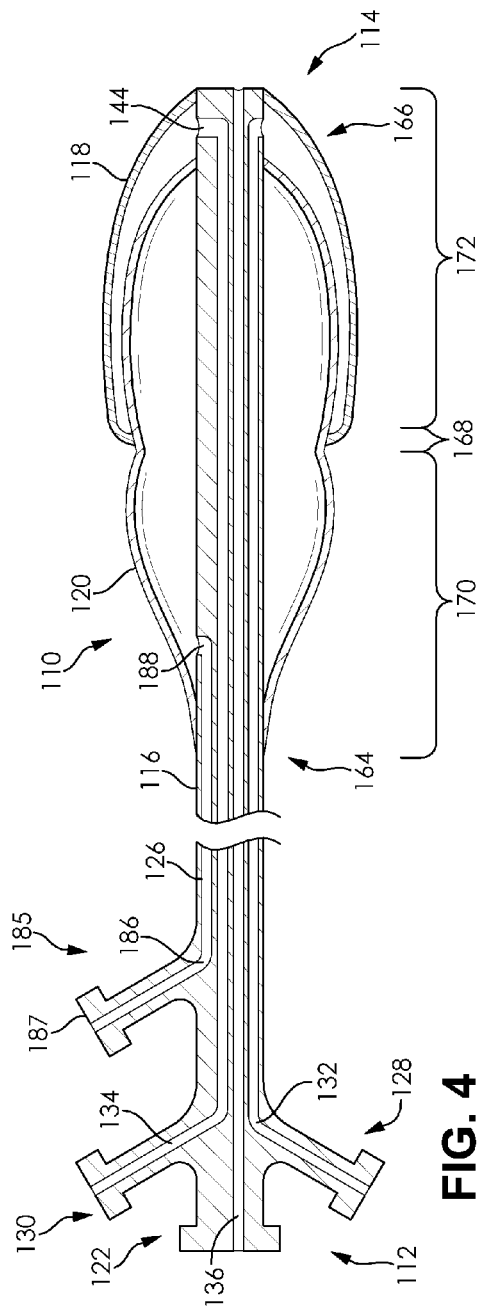

ARTICULATING BALLOON CATHETER AND METHOD FOR USING THE SAME

FIELD

The disclosure relates to medical devices. More particularly, the disclosure relates to balloon catheters useful in intraluminal treatment procedures on animals, such as human beings. The disclosure also relates to methods of using catheters.

BACKGROUND

Currently known catheters present challenges when being used in locations of the body that include distinct spaces, such as the distinct vascular spaces present within an arteriovenous fistula (AVF) and the distinct vascular and graft spaces present within an arteriovenous graft (AVG). As a result, a need remains for new catheters that are adapted to perform in body locations that require bridging between distinct spaces.

DESCRIPTION OF FIGURES

FIG. 2 is a longitudinal sectional view of the articulating balloon catheter illustrated in FIG. 1.

FIG. 2A is a magnified view of area 2A indicated in FIG. 2.

FIG. 3 is a magnified partial side view of the distal end of the articulating balloon catheter illustrated in FIG. 1 in a second configuration.

FIG. 4 is a longitudinal sectional view of another articulating balloon catheter.

DESCRIPTION OF EMBODIMENTS

Figure 1:
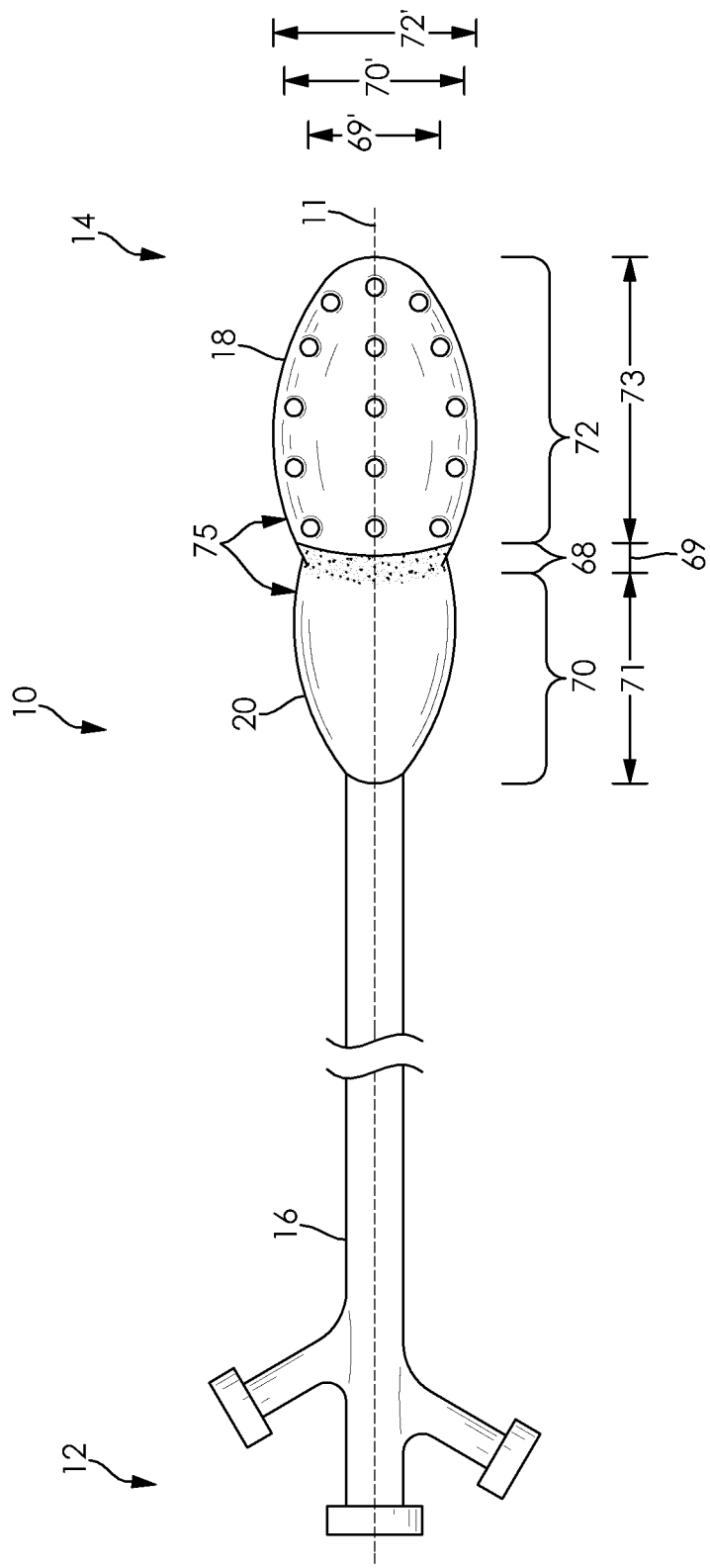
FIG. 1 is a side view of an articulating balloon catheter in a first configuration.

The following detailed description and the appended drawings describe and illustrate various example embodiments of medical devices and methods of treatment. The description and illustration of these examples are provided to enable one skilled in the art to make and use a medical device and to practice a method of treatment using a medical device according to an embodiment. They are not intended to limit the scope of the claims in any manner.

The use of "e.g.," "etc.," "for instance," "in example," and "or" and grammatically related terms indicate non-exclusive alternatives without limitation, unless otherwise noted. The use of "optionally" and grammatically related terms means that the subsequently described element, event, feature, or circumstance may or may not be present or occur, and that the description includes instances where said element, event, feature, or circumstance occurs and instances where it does not. The use of "attached" refers to the fixed, releasable, or integrated association of two or more elements and/or devices. Thus, the term "attached" includes releasably attaching or fixedly attaching two or more elements and/or devices. As used herein, the terms "proximal" and "distal" are used to describe opposing axial ends of the particular element or feature being described. The use of "diameter" refers to the length of a straight line passing from side to side through the center of a body, element, or feature, and does not impart any structural configuration on the body, element, or feature.

The term "bioactive" refers to any substance that can be introduced into a patient for a desired effect. Examples of suitable bioactive substances include anti-proliferatives, such as paclitaxel, thymosins, anti-inflammatories, such as dexamethasone, anti-microbials, statins, -olimus drugs, such as sirolimus and everolimus, anticlotting agents, therapeutic agents, regenerative materials, regenerative cells, endothelial progenitor cells, drug carriers, gels, and any other substance considered suitable for a particular embodiment. Skilled artisans will be able to select a suitable bioactive substance for a particular embodiment based on various considerations, including the treatment intended to be performed.

The use of "bodily passage" or "body passage" refers to any passage within the body of an animal, including, but not limited to, humans, and includes, but is not limited to, elongate passages, arteries, veins, fistulas, and grafts.

The term "textile balloon" refers to a balloon that has a textile material disposed on a surface of the balloon, or within the material forming the balloon. The material can be any suitable material, such as nylon fibers, synthetic or natural nanofibers or microfibers, woven textile sleeves, and any other material considered suitable for a particular embodiment.

FIGS. 1, 2, 2A, and 3 illustrate an embodiment of an articulating balloon catheter 10 that has a lengthwise axis 11, a proximal end 12, a distal end 14, an elongate member 16, a first balloon 18, and a second balloon 20. The articulating balloon catheter 10 has a first configuration, illustrated in FIGS. 1, 2, and 2A, and a second configuration illustrated in FIG. 3. Movement of the articulating balloon catheter 10 between the first configuration and the second configuration is described in more detail herein.

In the illustrated embodiment, elongate member 16 comprises a proximal end 22, a distal end 24, and a body 26 that defines an infusion port 28, an inflation port 30, an infusion lumen 32, an inflation lumen 34, and a guide wire lumen 36.

The infusion port 28 and inflation port 30 are disposed on a proximal portion of elongate member 16 and can include any suitable connector and/or adapter capable of attaching one or more devices to elongate member 16. Skilled artisans will be able to select a suitable connector and/or adapter to include on an infusion port and/or inflation port of an elongate member according to a particular embodiment based on various considerations, including the materials that form the elongate member. Example connectors and/or adapters considered suitable to include on an infusion port and/or inflation port of an elongate member include threaded connectors, Tuohy Borst adapters, luer lock connectors, and any other connector and/or adapter considered suitable for a particular embodiment.

The infusion lumen 32 extends from a first opening 38 defined on infusion port 28 to a second opening 40 defined between the proximal end 22 and distal end 24 of elongate member 16. The inflation lumen 34 extends from a first opening 42 defined on inflation port 30 to a second opening 44 defined between the proximal end 22 and distal end 24 of elongate member 16. In the illustrated embodiment, the second opening 44 is disposed near the distal end 66 of the second balloon 20. The guide wire lumen 36 extends between a first opening 46 defined on the proximal end 22 of elongate member 16 to a second opening 48 defined on the distal end 24 of elongate member 16. Each of the guide wire lumen 36, first opening 46, and second opening 48 is sized and configured to receive a guide wire such that the articulating balloon catheter 10 can be advanced over the guide wire and toward a point of treatment within a bodily passage. This can be accomplished, for example, by using any suitable technique, including conventional techniques such as the Seldinger technique.

Movement of articulating balloon catheter 10 between the first configuration and the second configuration is accomplished by introducing a fluid into the inflation chamber 76 of the second balloon 20 and/or by advancing the articulating balloon catheter 10 over a guide wire, as described in more detail herein. When the articulating balloon catheter 10 is in the first configuration, such as illustrated in FIGS. 1, 2, and 2A, the elongate member 16 is straight. Alternatively, when an articulating balloon catheter 10 is in the first configuration, the elongate member 16 can be substantially straight. When the articulating balloon catheter 10 is in the second configuration, such as illustrated in FIG. 3, the elongate member 16 defines a curve between the proximal end 22 and the distal end 24 of the elongate member 16.

Elongate member 16 can have any suitable outside diameter and length, and skilled artisans will be able to select a suitable outside diameter and length for an elongate member according to a particular embodiment based on various considerations, including the desired bodily passage within which an articulating balloon catheter is intended to be used, and/or the structural arrangement of a balloon attached to the elongate member.

Elongate member 16 can be formed of any suitable material capable of allowing movement of the articulating balloon catheter 10 between the first configuration and the second configuration, as described herein. Skilled artisans will be able to select a suitable material to form an elongate member according to a particular embodiment based on various considerations, including the desired flexibility of the elongate member. Example materials considered suitable to form an elongate member include, but are not limited to, biocompatible materials, materials that can be made biocompatible, metals such as stainless steel, titanium, nickel-titanium alloy (e.g., Nitinol), polymers, Pebax (Pebax is a registered trademark of Ato Chimie Corporation of Allee des Vosges, Courbevoie, France), nylon, polyethylene, polyurethane, silicone, coiled materials, braided materials, and any other material considered suitable for a particular embodiment. Optionally, an elongate member can include coiled and/or braided materials disposed within, or on the exterior or interior of the wall of the elongate member to prevent kinking of the elongate member during use.

Optionally, an elongate member can be formed of a proximal portion and a distal portion. The proximal portion extends from the proximal end toward the distal end and the distal portion extends from the distal end toward the proximal end. The distal portion can be entirely disposed within a chamber defined by a balloon, or at least partially disposed within a chamber defined by a balloon. The proximal and distal portions of the elongate member can have any suitable structure, or be formed of any suitable material, such that the proximal portion is relatively more rigid than the distal portion. For example, the proximal portion can be formed of a first material and the distal portion can be formed of a second material. In this embodiment, the first material has a first elastic modulus and the second material has a second elastic modulus that is less than the first elastic modulus. Thus, the second material is relatively more flexible/less stiff than the first material. The term "elastic modulus," as used herein, includes any suitable modulus, such as Young's modulus, bulk modulus, and/or shear modulus. In another embodiment, the proximal portion can have a first outside diameter and the distal portion can have a second outside diameter that is less than the first outside diameter. Another embodiment comprises incorporating one or more fibers within the material that forms the proximal portion and/or distal portion, or attaching one or more fibers to a surface of the proximal portion and/or distal portion, such that the proximal portion has a first elastic modulus and the distal portion has a second elastic modulus that is less than the first elastic modulus. Thus, the proximal portion is relatively more rigid than the distal portion. For example, the proximal portion can include one or more fibers that have a first weave pattern, angle relative to the lengthwise axis of the elongate member, and/or density that is different than a second weave pattern, angle relative to the lengthwise axis of the elongate member, and/or density of one or more fibers included on the distal portion. Another embodiment comprises hot or cold drawing the polymer material that forms the proximal portion using a first technique during the manufacturing process and hot or cold drawing the material that forms the distal portion using a second technique during the manufacturing process. The first technique is different than the second technique such that the proximal portion has a first elastic modulus and the distal portion has a second elastic modulus that is less than the first elastic modulus. Thus, the distal portion is relatively more flexible/less stiff than the proximal portion. Any of the above-described embodiments can be utilized individually, or in combination with one or more other embodiments.

While elongate member 16 has been illustrated as defining an infusion port, inflation port, infusion lumen, inflation lumen, and guide wire lumen, an elongate member can have any suitable structural configuration defining any suitable number of ports and/or lumens. Skilled artisans will be able to select a suitable structural configuration and number of ports and/or lumens to include on an elongate member according to a particular embodiment based on various considerations, including the structural configuration of a first balloon and/or second balloon of an articulating balloon catheter. For example, alternative to defining an infusion port and an inflation port, as illustrated in FIGS. 1 and 2, an elongate member can comprise a straight, or substantially straight, elongate shaft that has a proximal end that defines a first opening that is in communication with an infusion lumen and/or a first opening that is in communication with an inflation lumen. Example number of lumens considered suitable to include in an elongate member include one, at least one, two, a plurality, three, four, five, and any other number considered suitable for a particular embodiment. For example, alternative to including a guide wire lumen, an elongate member can omit a guide wire lumen and define an infusion lumen and/or an inflation lumen.

In the illustrated embodiment, first balloon 18 comprises a proximal end 54, a distal end 56, and a wall 58 that defines a plurality of pores 60. The wall 58 of first balloon 18, the portion of the exterior surface of the elongate member 16 disposed within first balloon 18, and the exterior surface of the second balloon 20 define an infusion chamber 62. Second balloon 20 comprises a proximal end 64, a distal end 66, an articulating region 68, a proximal portion 70, a distal portion 72, and a wall 74. The wall 74 of second balloon 20, the portion of the exterior surface of the elongate member 16 disposed within second balloon 20, and the interior surface of the second balloon 20 define an inflation chamber 76.

The first balloon 18 is attached to second balloon 20 between the proximal end 64 and distal end 66 of the second balloon 20 at a proximal junction 78 and to the distal end 24 of the elongate member 16 at a distal junction 80. The proximal junction 78 is disposed distal to the articulating region 68 of the second balloon 20 such that the first balloon 18 is positioned over a portion of the second balloon 20. The first balloon 18 is attached to elongate member 16 such that the second opening 40 of the infusion lumen 32 is in communication with infusion chamber 62. With this structural arrangement, the first balloon 18 is adapted to move between a deflated configuration and an inflated configuration as fluid and/or a bioactive is moved into and out of the infusion chamber 62 via the infusion lumen 32 and/or when second balloon 20 is moved between a deflated configuration and an inflated configuration, as described in more detail herein. FIGS. 1, 2, and 2A illustrate the first balloon 18 in the deflated configuration and FIG. 3 illustrates the first balloon 18 in the inflated configuration. Optionally, in embodiments in which an infusion lumen has been omitted from the elongate member, the inclusion of a first balloon can be omitted. Embodiments that omit the inclusion of a first balloon facilitate the delivery of a device at a point of treatment (e.g., stent, mechanically expandable stent, graft). However, embodiments that include a first balloon can also be used to deliver a device at a point of treatment.

The second balloon 20 is attached to elongate member 16 between the proximal end 22 and distal end 24 of the elongate member 16 at a proximal junction 82 and a distal junction 84. A portion of the distal portion 72 of the second balloon 20 is disposed radially inward of first balloon 18, as shown in FIGS. 1, 2, and 2A. Alternatively, the entire second balloon of an articulating balloon catheter can be disposed radially inward of a first balloon such that the first balloon has a proximal end attached to an elongate member. The second balloon 20 is attached to the elongate member 16 such that the second opening 44 of the inflation lumen 34 is in communication with the inflation chamber 76. With this structural arrangement, the second balloon 20 is adapted to move between a deflated configuration and an inflated configuration as fluid is moved into and out of inflation chamber 76 via the inflation lumen 34. FIGS. 1, 2, and 2A illustrate the second balloon 20 in the deflated configuration and FIG. 3 illustrates the second balloon 20 in the inflated configuration.

The proximal junction 78 between the first balloon 18 and second balloon 20 can comprise any suitable method of attachment between a first balloon and a second balloon, and skilled artisans will be able to select a suitable method of attachment between a first balloon and a second balloon according to a particular embodiment based on various considerations, including the material(s) that form the first balloon and the second balloon. Example methods of attachment considered suitable between a first balloon and a second balloon include attachments formed by heat fusing, using adhesives, mechanical connections, and any other method considered suitable for a particular embodiment.

Each of the distal junction 80, proximal junction 82, and distal junction 84 can comprise any suitable method of attachment between a balloon and an elongate member. Skilled artisans will be able to select a suitable method of attachment between a balloon and an elongate member according to a particular embodiment based on various considerations, including the material(s) that form the elongate member and the balloon. Example methods of attachment considered suitable between an elongate member and a balloon include, but are not limited to, attachments formed by heat fusing, using adhesives, mechanical connections, and any other method of attachment considered suitable for a particular embodiment.

While the first balloon 18 has been illustrated as attached to the second balloon 20 between the proximal end 64 and distal end 66 of the second balloon 20 and at the distal end 24 of the elongate member 16, a first balloon can be attached to a second balloon and/or an elongate member at any suitable location along the length of a second balloon and/or an elongate member. Skilled artisans will be able to select a suitable location to attach a first balloon to a second balloon and/or an elongate member according to a particular embodiment based on various considerations, including the structural arrangement of the elongate member, or the structural arrangement of the second balloon. Example locations considered suitable to attach a first balloon to a second balloon include at the proximal end of the second balloon, between the proximal end and distal end of the second balloon, at the distal end of the second balloon, proximal to the articulating region of the second balloon, on the articulating region of the second balloon, distal to the articulating region of the second balloon, and any other location considered suitable for a particular embodiment. Example locations considered suitable to attach a first balloon to an elongate member include at the distal end of the elongate member, between the proximal end and distal end of the elongate member, adjacent the distal end of the second balloon, between the proximal and distal ends of the second balloon, and any other location considered suitable for a particular embodiment. For example, a second balloon can have a distal end attached to a first balloon.

While second balloon 20 has been illustrated as attached to elongate member 16 between the proximal end 22 and distal end 24 of the elongate member 16, a second balloon can be attached to an elongate member at any suitable location along the length of the elongate member. Skilled artisans will be able to select a suitable location to attach a balloon to an elongate member according to a particular embodiment based on various considerations, including the structural arrangement of the elongate member and/or the balloon. Example locations considered suitable to attach a balloon to an elongate member include between the proximal end and distal end of the elongate member, at the distal end of the elongate member, and any other location considered suitable for a particular embodiment.

Each pore of the plurality of pores 60 extends through the wall 58 of the first balloon 18 and provides access to the infusion chamber 62 such that when a fluid and/or bioactive is introduced into the infusion chamber 62 it can be passed through each pore of the plurality of pores 60, or a portion of the plurality of pores 60. This facilitates the introduction of a bioactive into a bodily passage, or into the wall of a bodily passage, as described in more detail herein.

Any suitable bioactive can be passed through a pore of the plurality of pores 60, and skilled artisans will be able to select a suitable bioactive according to a particular embodiment based on various considerations, including the treatment intended to be performed. Example bioactives considered suitable to pass through a pore of a balloon of an articulating balloon catheter include those described herein, anti-proliferatives, such as paclitaxel, thymosins, anti-inflammatories, such as dexamethasone, anti-microbials, statins, -olimus drugs, such as sirolimus and everolimus, agents, anticlotting agents, therapeutic agents, regenerative materials, regenerative cells, endothelial progenitor cells, drug carriers, gels, and any other substance considered suitable for a particular embodiment.

While a plurality of pores 60 has been illustrated as defined by the wall 58 of the first balloon 18, the wall of a balloon can define any suitable number of pores. Skilled artisans will be able to select a suitable number of pores to include on a balloon according to a particular embodiment based on various considerations, including the desired amount of a bioactive intended to be delivered at a point of treatment. Example number of pores considered suitable to include on a balloon include one, at least one, two, a plurality, three, four, five, six, seven, eight, nine, ten, eleven, twelve, thirteen, fourteen, fifteen, and any other number considered suitable for a particular embodiment.

Each pore of the plurality of pores 60 can have any suitable diameter and structural configuration, and skilled artisans will be able to select a suitable diameter and structural configuration for a pore according to a particular embodiment based on various considerations. Example diameters considered suitable include each pore of a plurality of pores having the same diameter, a first pore of a plurality of pores having a first diameter and a second pore of the plurality of pores having a second diameter that is different than the first diameter, each pore in a first set of pores of a plurality of pores having a first diameter and each pore in a second set of pores of the plurality of pores having a second diameter that is different than the first diameter, and any other diameter considered suitable for a particular embodiment. For example, when at least two pores are provided, at least two of the pores can have different diameters. Example structural configurations considered suitable for a pore include a pore that has a continuous diameter from a first opening to a second opening, a pore that has a diameter that varies from a first opening to a second opening, a pore that has a diameter that tapers from a first opening to a second opening, a pore that has a diameter that tapers from a second opening to a first opening, a pore that has a diameter that is curved from a first opening to a second opening, and any other structural configuration considered suitable for a particular embodiment.

Optionally, a first balloon and/or second balloon, or one or more portions thereof (e.g., articulating region, proximal portion, distal portion), can include one or more micro-needles. The one or more micro-needles can be attached to the exterior surface of the balloon such that they extend away from the exterior surface of the balloon. Alternatively, the one or more micro-needles can move between a first configuration and second configuration. In the first configuration, when the balloon is in the deflated configuration, the one or more micro-needles are entirely, or partially, disposed within the wall of the balloon. Thus, in the first configuration, a first length of each micro-needle of the one or more micro-needles is disposed within the wall of the balloon. The first length is measured along an axis that is transverse to the lengthwise axis of the balloon. In the second configuration, when the balloon is in the inflated configuration, the one or more micro-needles extend from the exterior surface of the wall of the balloon. Thus, in the second configuration, a second length of each micro-needle of the one or more micro-needles is disposed within the wall of the balloon. The second length is measured along an axis that is transverse to the lengthwise axis of the balloon and is less than the first length. The one or more micro-needles can have any structure capable of penetrating the wall of a bodily passage. For example, each of the one or more micro-needles can comprise a shaft, or tubular member, that has a sharp end disposed opposite the end attached to the exterior surface of the balloon. In embodiments in which one or more tubular micro-needles are attached to the exterior surface of a balloon, at least one of the one or more micro-needles can optionally be positioned over a pore of the plurality of pores such that a fluid and/or bioactive can be delivered into the tissue that forms the wall of a bodily passage through the at least one micro-needle.

In the illustrated embodiment, the articulating region 68 is disposed between the proximal portion 70 and the distal portion 72 of the second balloon 20. The articulating region 68 has a length 69 and extends about the entire circumference of the second balloon 20 such that in the inflated configuration, as illustrated in FIG. 3, the distal portion 72 is disposed at an angle to the proximal portion 70. The proximal portion 70 extends from the proximal end 64 of the second balloon 20 to the proximal end of the articulating region 68 and has a length 71. The distal portion 72 extends from the distal end of the articulating region 68 to the distal end 66 of the second balloon 20 and has a length 73. Each of the length 69 of the articulating region 69, the length 71 of the proximal portion 70, and the length 73 of the distal portion 72 is measured along the lengthwise axis 11. In the embodiment illustrated in FIGS. 1, 2, 2A, and 3, the length 69 of the articulating region 68 is less than the length 71 of the proximal portion 70 and the length 73 of the distal portion 72.

Articulating region 68 can comprise any suitable structure capable of providing articulation between the proximal portion 70 and distal portion 72 of the second balloon 20 when the second balloon 20 moves between the deflated and inflated configurations and/or as the articulating balloon catheter 10 is advanced over a guide wire. Skilled artisans will be able to select a suitable structure for an articulating region according to a particular embodiment based on various considerations, including the desired amount of articulation between the proximal portion and the distal portion of a balloon. Example structures considered suitable for an articulating region of a balloon include positioning one or more restraining bands and/or stents within the wall of a balloon or on a surface (e.g., exterior, interior) of the balloon, positioning a corrugated material within the wall of a balloon or on a surface (e.g., exterior, interior) of the balloon, forming a balloon such that the articulating region is corrugated, incorporating one or more fibers into a portion, or the entirety, of the material forming the balloon, attaching one or more fibers onto a portion, or the entirety, of a surface of the balloon, varying the thickness of the wall of a balloon, processing the balloon to alter the material properties of a portion, or the entirety, of the balloon (e.g., impart stiffness to the articulating region), and any other structure considered suitable for a particular embodiment. Thus, articulating region 68 can comprise a portion of second balloon 20 or another element or feature attached to, or disposed within the wall 74, of the second balloon 20.

In the illustrated embodiment, the articulating region 68 is formed of a first material, the proximal portion 70 is formed of a second material, and the distal portion 72 formed of a third material. The first material is the same as the second material and the third material. The first material has a first elastic modulus, the second material has a second elastic modulus, and the third material has a third elastic modulus. The first elastic modulus is greater than the second elastic modulus and the third elastic modulus. Thus, the first material is relatively more rigid than the second material and the third material. With this structural arrangement, articulation between the proximal portion 70 and the distal portion 72 can be accomplished by inflating and deflating the second balloon 20 and/or advancing the articulating balloon catheter 10 over a guide wire, as described herein. For example, when a fluid is introduced into the inflation chamber 76 of the second balloon 20 the first material forming the articulating region 68 expands such that is has an outside diameter that is less than the expanded outside diameter of the second material and the third material, which allows articulation between the proximal portion 70 and the distal portion 72 of the second balloon 20. Alternatively, the material forming an articulating region can be formed of a first material that is different than the second material that forms the proximal portion and/or the third material that forms the distal portion of a balloon.

In embodiments in which the articulating region comprises a stent disposed within the wall of a balloon or on a surface of the balloon (e.g., FIG. 7), any suitable stent that has any structural configuration can be used. Skilled artisans will be able to select a suitable stent and a suitable structural configuration for a stent according to a particular embodiment based on various considerations, including the desired amount of articulation between the proximal portion and distal portion of a balloon. For example, a stent can comprise a self-expandable or mechanically expandable stent. A stent can be formed of any suitable material including, but not limited to, biocompatible materials, materials that can be made biocompatible, metals, stainless steel, nickel titanium (NiTi) alloys (e.g., nitinol), shape memory materials, superelastic materials, molybdenum alloys, tantalum alloys, titanium alloys, precious metal alloys, nickel chromium alloys, cobalt chromium alloys, nickel cobalt chromium alloys, nickel cobalt chromium molybdenum alloys, nickel titanium chromium alloys, polymers, composite materials, and any other material considered suitable for a particular embodiment. A stent can have any suitable structural arrangement including, but not limited to, a closed-cell stent, z-stent, and any other structural arrangement considered suitable for a particular embodiment.

In embodiments in which one or more fibers have been incorporated into a portion, or the entirety, of the material forming the balloon and/or have been attached to a surface of the balloon, any suitable fiber can be used. Skilled artisans will be able to select a suitable fiber, structural arrangement for a fiber, and/or material for a fiber according to a particular embodiment based on various considerations, including the material(s) that form a balloon. Example materials considered suitable for a fiber include polymers, nylon, metals, and any other material considered suitable for a particular embodiment.

For example, a balloon can comprise one or more fibers that are attached to the surface of a balloon and/or incorporated within the material that forms the balloon. Any suitable portion of a balloon, such as the articulating region, proximal portion, and/or distal portion, can include one or more fibers such that the articulating region has an elastic modulus that is greater than the proximal portion and/or the distal portion (e.g., the articulating region is relatively more rigid than the proximal portion and/or the distal portion). The one or more fibers incorporated into, or attached to the surface of, the material that forms the articulating region can have a first configuration and the one or more fibers incorporated into, or attached to the surface of, the material that forms the proximal portion and/or distal portion can have a second configuration that is different than the first configuration. The first and/or second configuration can comprise any suitable weave/braid pattern of the one or more fibers, angular positioning of the one or more fibers relative to the lengthwise axis of the balloon, and/or density of the one or more fibers.

In embodiments in which the balloon includes a wall that has a thickness that varies along the length of the balloon, the portion of the wall that forms the articulating region can have a first thickness, the portion of the wall that forms the proximal portion can have a second thickness, and the portion of the wall that forms the distal portion can have a third thickness. The first thickness is greater than the second thickness and the third thickness such that the articulating region has an elastic modulus that is greater than the proximal portion and/or distal portion (e.g., the articulating region is relatively more rigid than the proximal portion and/or the distal portion).

In embodiments in which a corrugated material has been positioned within the wall of a balloon or on a surface (e.g., exterior, interior) of the balloon, the corrugated material can comprise any suitable material, such as a polymer (e.g., polyester). Alternatively, in embodiments in which the articulating region of a balloon is formed such that it is corrugated, any suitable method of achieving a corrugated region can be used. For example, a corrugated region can be defined on a balloon by heat setting the articulating region on a mandrel during the manufacturing process or during a blow molding process in which the balloon is disposed in a molding that defines the corrugated region. Alternatively, the corrugated region can be defined by one or more fibers that are attached about the circumference of the balloon such that in the inflated configuration, each of the one or more fibers constrains the outside diameter of the balloon to define the corrugated region.

Processing of a balloon to alter the material properties of the balloon (e.g., impart stiffness), or a portion of the balloon (e.g., articulating region), can be accomplished using any suitable technique and at any suitable time in the manufacturing of an articulating balloon catheter, such as before and/or after securement of the balloon to the elongate member. Skilled artisans will be able to select a suitable technique to process a balloon to alter its material properties according to a particular embodiment based on various considerations, including the material(s) that form the balloon. For example, any suitable technique capable of inducing orientation and/or crystallinity in the polymer material of the balloon, or a portion thereof (e.g., articulating region 68, proximal portion 70, distal portion 72) can be used. Example techniques considered suitable to alter the material properties (e.g., impart stiffness) of a balloon, or a portion of a balloon (e.g., articulating region 68, proximal portion 70, distal portion 72), include applying solvents, cross-linking, ion beam bombardment, targeted heating, targeted heating and annealing, biased radial expansion while the balloon, or portion of the balloon, is being heated, stretching the balloon along its length, or portion of its length (e.g., articulating region 68, proximal portion 70, distal portion 72), while it is being cooled, and any other technique capable of altering the material properties of the balloon. For example, the proximal and/or distal portions of a balloon (e.g., proximal portion 70, distal portion 72) can be masked such that the articulating region (e.g., articulating region 68) is exposed. Any suitable material can be used to mask the proximal portion and/or distal portion of a balloon, such as biaxially-oriented polyethylene terephthalate (BoPET) (e.g., Mylar (Mylar is a registered trademark of E.I. Du Pont De Nemours and Company Corporation of Wilmington, Del.)). Subsequently, one of the techniques described herein, or any other suitable technique, can be completed such that the material properties of the articulating region of the balloon are altered. For example, a solvent (e.g., methyl chloride) can be applied to a balloon, such as a balloon that is formed of a polymer (e.g., nylon), such that the material properties of the balloon are altered (e.g., the polymer chain is reoriented, orientation and crystallinity are increased).

Alternative to masking a portion of the balloon to alter its material properties, the balloon can have an articulating region formed of a first material, a proximal portion formed of a second material, and a distal portion formed of a third material. The first material can be different than the second material and the third material such that it reacts differently to one or more of the techniques described herein (e.g., application of a solvent, ion beam, targeting heating, targeting heating and annealing) to accomplish a balloon with an articulating region. When the material properties of the articulating region of a balloon have been altered such that the material that forms the articulating region has an elastic modulus that is greater than the material that forms the proximal portion and/or the distal portion (e.g., the material that forms the articulating region is relatively more rigid than the material that forms the proximal portion and/or distal portion), the articulating region will resist expansion and create articulation between the proximal portion and the distal portion of the balloon when it is moved between the inflated and deflated configurations and/or advanced over a guide wire.

While articulating region 68 has been illustrated as having a length 69 and such that it extends about the entire circumference of the second balloon 20, an articulating region of a balloon can have any suitable length and extend about any suitable portion of the circumference of a balloon. Skilled artisans will be able to select a suitable length for an articulating region and a suitable portion of the articulating region to extend about the circumference of a balloon according to a particular embodiment based on various considerations, including the amount of articulation desired between a proximal portion and a distal portion of the balloon. For example, an articulating region of a balloon can have a length that is equal to, substantially equal to, greater than, or less than the length of a proximal portion and/or distal portion of the balloon. Alternative to an articulating region extending about the entire circumference of a balloon, an articulating region can extend about a portion of the circumference of a balloon.

While articulating balloon catheter 10 has been illustrated as including a single articulating region 68, a balloon included on an articulating balloon catheter can comprise any suitable number of articulating regions, such as those described herein. Skilled artisans will be able to select a suitable number of articulating regions to include on a balloon according to a particular embodiment based on various considerations, including the desired inflated configuration of a balloon. Example number of articulating regions to include on a balloon of an articulating balloon catheter include one, at least one, two, a plurality, three, four, five, six, seven, and any other number considered suitable for a particular embodiment. For example, a balloon can comprise a first articulating region disposed proximal to a second articulating region. The first articulating region can comprise a first structure and the second articulating region can comprise a second structure that is the same as, or different than, the first structure.

In use, first balloon 18 is moved between the deflated and inflated configuration by way of movement of second balloon 20 between its deflated configuration and inflated configuration. The second balloon 20 is inflated by introducing a fluid, such as saline, into first opening 42, through the inflation lumen 34 and second opening 44, and into the inflation chamber 76. The resulting pressure placed on the inner surface of second balloon 20 by the fluid causes first balloon 18 and second balloon 20 to inflate and adopt the inflated configuration, as illustrated in FIG. 3. To move first balloon 18 and second balloon 20 to their deflated configurations, vacuum pressure is applied to inflation lumen 34 (e.g., using a syringe) to remove fluid located within the inflation chamber 76 through the second opening 44, inflation lumen 34, and first opening 42, which results in the first balloon 18 and second balloon 20 collapsing and adopting the deflated configurations.

In the deflated configuration, as illustrated in FIGS. 1, 2, and 2A, the proximal portion 70 of the second balloon 20 is disposed at an angle 75 to the distal portion 72 of second balloon 20 and the elongate member 16 is straight. The angle 75 is equal to about 180 degrees. In the inflated configuration, as illustrated in FIG. 3, the proximal portion 70 of the second balloon 20 is disposed at a second angle 75' to the second portion 72 of the second balloon 20 and the elongate member 16 defines a curve along its length. Thus, articulation between the proximal portion 70 and the distal portion 72 dominates the structural configuration of elongate member 16. The second angle 75' is equal to about 135 degrees. As the second balloon 20 is moved from the deflated configuration to the inflated configuration, the pressure within inflation chamber 76 increases resulting in the distal portion 72 articulating relative to the proximal portion 70. This is accomplished based on the structural arrangement of articulating region 68 and the flexibility of the elongate member 16.

While particular angles have been illustrated as defined between the proximal portion 70 and the distal portion 72 when the second balloon is in the deflated configuration and the inflated configuration, any suitable angle can be defined between the proximal portion and the distal portion of an articulating balloon catheter when a balloon is in the deflated configuration or inflated configuration. Skilled artisans will be able to select suitable angle to define between a proximal portion and a distal portion of a balloon when the balloon is in the deflated configuration or inflated configuration according to a particular embodiment based on various considerations, including the structural arrangement at an intended point of treatment. Example angles considered suitable to define between a proximal portion and a distal portion of a balloon when the balloon is in the inflated configuration include 45 degrees, about 45 degrees, 90 degrees, about 90 degrees, 135 degrees, about 135 degrees, 180 degrees, about 180 degrees, angles that facilitate articulation between the proximal portion and the distal portion of a balloon when the balloon is moved between the deflated and inflated configurations, and any other angle considered suitable for a particular embodiment. For example, the second balloon can omit the inclusion of a predefined angle between the proximal portion and the distal portion when it is in the inflated configuration such that the second balloon and elongate member are straight, or substantially straight, when the second balloon is in the inflated configuration and free of a wire guide.

In the deflated configuration, the articulating region 69 has a first outside diameter 69', the proximal portion 70 has a first outside diameter 70', and the distal portion 72 has a first outside diameter 72'. The first outside diameter 70' of the proximal portion 70 is equal to the first outside diameter 72' of the distal portion 72 and is greater than the first outside diameter 69' of the articulating region 69. In the inflated configuration, the articulating region 69 has a second outside diameter 69", the proximal portion 70 has a second outside diameter 70", and the distal portion 72 has a second outside diameter 72". The second outside diameter 70" of the proximal portion 70 is equal to the second outside diameter 72" of the distal portion 72 and is greater than the second outside diameter 69" of the articulating region 69.

While various first and second outside diameters have been illustrated with respect to the articulating region 69, proximal portion 70, and distal portion 72, the articulating region, proximal portion, and distal portion of a balloon can have any suitable outside diameter in the deflated configuration or inflated configuration. Skilled artisans will be able to select a suitable outside diameter for the articulating region, proximal portion, and/or distal portion of a balloon according to a particular embodiment based on various considerations, including the bodily passage(s) in which an articulating balloon catheter is intended to be used. Example outside diameters considered suitable for a balloon include the proximal portion of the balloon having an outside diameter that is equal to, greater than, or less than, the outside diameter of the distal portion and/or the articulating region of the balloon when the balloon is in the deflated configuration, the proximal portion of the balloon having an outside diameter that is equal to, greater than, or less than, the outside diameter of the distal portion and/or the articulating region of the balloon when the balloon is in the inflated configuration, the proximal portion of the balloon having an outside diameter that is substantially equal to the outside diameter of the distal portion and/or the articulating region of the balloon when the balloon is in the deflated configuration, the proximal portion of the balloon having an outside diameter that is substantially equal to the outside diameter of the distal portion and/or the articulating region of the balloon when the balloon is in the inflated configuration, the proximal portion of the balloon having an outside diameter that is different than the outside diameter of the distal portion and/or the articulating region of the balloon when the balloon is in the deflated configuration, the proximal portion of the balloon having an outside diameter that is different than the outside diameter of the distal portion and/or the articulating region of the balloon when the balloon is in the inflated configuration, and any other diameter considered suitable for a particular embodiment.

Treatment can be performed by introducing a portion, or the entirety, of the distal end 24 of the elongate member 16, first balloon 18, and second balloon 20 into a bodily passage. Subsequently, second balloon 20 can be moved to an inflated configuration such that the distal portion 72 articulates relative to the proximal portion 70 to define second angle 75' within the bodily passage. Alternatively, the articulating balloon catheter 10 can be advanced over a guide wire such that the guide wire dominates the structural arrangement of the articulating balloon catheter 10 (e.g., the balloon does articulate relative to the elongate member when it is in the inflated configuration). Articulating balloon catheter 10 provides a mechanism for responding to the anatomy of one or more bodily passages without dominating the structural arrangement of the anatomy of the one or more bodily passages. For example, the distal portion can be disposed within a first bodily passage and the proximal portion can be disposed within a second bodily passage that is in communication with the first bodily passage. Alternatively, the proximal portion of a balloon can be disposed in a first portion of a bodily passage and the distal portion of the balloon can be disposed within a second portion of the bodily passage. Prior to, during, or subsequent to the inflation of second balloon 20, a bioactive can be passed through the infusion lumen 32 and into infusion chamber 62 such that the bioactive is passed through each pore of the plurality of pores 60, or a portion of the plurality of pores 60.

By positioning the second opening 44 of the inflation lumen 34 near the distal end 66 of the second balloon 20 (e.g., between the distal end 66 of the second balloon 20 and the articulating region 68), the second balloon 20 can be inflated in stages such that the distal portion 72 is inflated at a rate that is greater than the rate at which the proximal portion 70 is inflated.

Alternative to, or in addition to, positioning the second opening 44 of the inflation lumen 34 near the distal end 66 of the second balloon 20 to accomplish staged inflation of the second balloon 20, any other suitable structure or technique can be used to accomplish staged inflation such that the distal portion is inflated at a rate that is greater than the rate at which the proximal portion is inflated, or vice versa. Example structures and techniques considered suitable to accomplish staged inflation include altering the material properties of the proximal portion (e.g., proximal portion 70) and/or distal portion (e.g., distal portion 72) of a balloon such that the proximal portion has an elastic modulus that is greater than the elastic modulus of the distal portion (e.g., the proximal portion is relatively more rigid than the distal portion), positioning a valve within the chamber defined by a balloon, positioning a sheath about the circumference of a portion of the balloon (e.g., proximal portion, articulating region) during use, defining two separate chambers within the balloon, and any other structure or technique considered suitable for a particular embodiment. Any suitable technique can be used to alter the material properties of the proximal portion and/or distal portion of a balloon, such as those described herein with respect to altering the material properties of the articulating region of a balloon. In embodiments that include a valve disposed within the chamber defined by the balloon, the valve can comprise any structure capable of maintaining a first pressure within a first portion of the chamber disposed distal to the valve and a second pressure within a second portion of the chamber disposed proximal of the valve. As pressure within the first portion reaches a predetermined value the valve opens and allows fluid to pass from the first portion to the second portion of the chamber. In embodiments in which a sheath is used to achieve staged inflation, the sheath can be disposed over the articulating balloon catheter while it is being advanced into a first and/or second bodily passage and withdrawn proximally over the articulating balloon catheter in stages. A first stage comprises withdrawing the sheath such that at least a portion of the distal portion of the balloon is disposed outside of the sheath. The second stage comprises withdrawing the sheath such that at least a portion of the articulating region is disposed outside of the sheath. The third stage comprises withdrawing the sheath such that at least a portion of the proximal portion is disposed outside of the sheath. In embodiments in which the balloon defines two separate chambers, a first chamber is disposed proximal to the second chamber and the elongate member defines a first inflation lumen in communication with the first chamber and a second inflation lumen in communication with the second chamber. Alternatively, two separate balloons, a first balloon disposed proximal to a second balloon, can be used to define the first and second chambers. Each of the first balloon and second balloon is attached to the elongate member. In embodiments in which two separate balloon are used, the chamber of the first balloon is in communication with a first inflation lumen defined by the elongate member and the chamber defined by the second balloon is in communication with a second inflation lumen defined by the elongate member.

While the second opening 44 of inflation lumen 34 has been illustrated as disposed near the distal end 66 of the second balloon 20, the second opening of an inflation lumen can be disposed at any suitable location along the length of an elongate member. Skilled artisans will be able to select a suitable location to position the second opening of an inflation lumen according to a particular embodiment based on various considerations, including the structural arrangement of the balloon that defines a chamber in communication with the second opening. For example, the second opening of an inflation lumen can be disposed between the articulating region and distal end of a balloon, between the proximal end and the articulating region of the balloon, between the proximal end of the articulating region and the distal end of the articulating region, and any other location considered suitable for a particular embodiment. Alternatively, an inflation lumen can extend from a proximal opening to a first distal opening and a second distal opening that is disposed distal to the first distal opening. Alternatively, an elongate member can define a first inflation lumen and a second inflation lumen. Each of the first inflation lumen and the second inflation lumen has a second opening in communication with the inflation chamber defined by a balloon.

First balloon 18 and second balloon 20 can be formed of any suitable material, and skilled artisans will be able to select a suitable material to form a first balloon and/or a second balloon according to a particular embodiment based on various considerations, including the materials that form an elongate member. Example materials considered suitable to form a balloon include biocompatible materials, materials that can be made biocompatible, flexible materials, substantially flexible materials, polymers, Pebax (Pebax is a registered trademark of Ato Chimie Corporation of Allee des Vosges, Courbevoie, France), nylon, polyethylene, polyurethane, nanofibers, and textile sleeves. In the embodiment illustrated in FIGS. 1, 2, 2A, and 3, the first balloon 18 is formed of a first material and the second balloon 20 is formed of a second material and each of the first balloon 18 and second balloon 20 is a non-compliant balloon. The first material is the same as the second material. Alternatively, the first material can be different than the second material and/or each of the first balloon and second balloon of an articulating balloon catheter can be a compliant balloon. Optionally, a balloon included in an articulating balloon catheter can be oversized any suitable value. For example, a balloon can be oversized 20%, or about 20%, between 1% and 20%, between about 1% and about 20%, and any other value considered suitable for a particular embodiment.

An example balloon considered suitable to include in an articulating balloon catheter (e.g., first balloon, second balloon) comprises a high-pressure balloon that has a rated burst pressure (RBP) between about 15 ATM and about 30 ATM. RBP is the statistically determined maximum pressure to which a balloon may be inflated without rupturing. The inventors have determined that balloons that are 20% oversized and/or that have a RBP of about 30 ATM are considered suitable for procedures in which fistula lesions are being treated.

Each of the first balloon 18 and second balloon 20 can have any suitable outside diameter and length, and skilled artisans will be able to select a suitable outside diameter and length for a balloon according to a particular embodiment based on various considerations, including the desired bodily passage within which an articulating balloon catheter is intended to be used. Example diameters considered suitable for a balloon include diameters between 7 millimeters and 9 millimeters, between about 7 millimeters and about 9 millimeters, and any other diameter considered suitable for a particular embodiment.

Optionally, a balloon included in an articulating balloon catheter can be formed as a textile balloon such that one or more textile materials are disposed on a surface of the balloon (e.g., articulating region, proximal portion, distal portion), or within the material forming the balloon (e.g., articulating region, proximal portion, distal portion). For example, one approach to accomplishing this structural arrangement is to deposit polymer nanofibers onto a balloon's surface using an electrospinning process, such as is described in U.S. Publ. Pat. App. 2008/0157444 by Melsheimer, which is incorporated by reference herein in its entirety. Another approach to accomplishing this structural arrangement is to include a seamlessly woven textile sleeve around a balloon, such that a thin-walled balloon device with a high RBP is formed. Examples of this structural arrangement are described in U.S. Publ. Pat. App. 2011/0046654 by Kuppurathanam, which is incorporated by reference herein in its entirety.

Optionally, an articulating balloon catheter can include one or more markers to facilitate tracking and positioning of the articulating balloon catheter during use. Example locations considered suitable to position a marker include at the proximal end of a balloon, at the distal end of a balloon, between the proximal end and the distal end of a balloon, at the proximal end of an articulating region of a balloon, at the distal end of an articulating region of a balloon, between the proximal end and the distal end of an articulating region of a balloon, at the distal end of an elongate member, between the proximal end and the distal end of an elongate member, at a pore defined by the wall of a balloon, proximal to a first pore defined by the wall of a balloon and distal to a second pore defined by the wall of the balloon, and any other location considered suitable for a particular embodiment. For example, a first marker can be disposed at the proximal end of a balloon, a second marker can be disposed at the distal end of the balloon, and a third marker can be disposed along the length of the articulating region of the balloon.

Any suitable marker can be included on an articulating balloon catheter, and skilled artisans will be able to select a suitable marker according to a particular embodiment based on various considerations, including the material(s) that forms the articulating balloon catheter. Example markers considered suitable include markers that can be located through visual examination of an articulating balloon catheter or through ultrasound technology, echogenic markers, radiopaque markers, and any other marker considered suitable for a particular embodiment. Examples of suitable radiopaque materials that can be used to form a radiopaque marker include cadmium, tungsten, gold, tantalum, bismuth, platinum, iridium, rhodium, and any other material considered suitable for a particular embodiment. The visualization, tracking, and/or positioning of an articulating balloon catheter can be accomplished using any suitable technique, and skilled artisans will be able to select a suitable technique according to a particular embodiment based on various considerations, such as the desired bodily passage within which an articulating balloon catheter is intended to be deployed. Example techniques considered suitable to facilitate visualization, tracking, and/or positioning of an articulating balloon catheter include x-ray, fluoroscopy, ultrasound, direct visualization with a scope, and magnetic resonance imaging.

Additional structure can be attached to the articulating balloon catheter 10 to facilitate the inflation and deflation of first balloon 18 and/or second balloon 20 or the introduction of a bioactive into the chamber of the first balloon 18, as described herein. For example, a syringe (not illustrated) or other suitable structure can be attached to the infusion port 28 and/or inflation port 30 using any suitable connection, such as a luer lock connection. A fluid or bioactive can be stored within the syringe, infusion lumen 28, and/or inflation lumen 30, and can be introduced into and removed from the infusion chamber 62 and/or inflation chamber 76 by operating the syringe using conventional practices.

Optionally, one or more articulating balloon catheters can be included in a kit. A first articulating balloon catheter can have a first structural configuration and a second articulating balloon catheter can have a second structural configuration that is different than the first. Each of the first and second articulating balloon catheters can have any suitable structural arrangement, such as those described herein, and can have any suitable articulating region, such as those described herein. Optional components that can be included in a kit include one or more syringes, one or more wire guides, one or more sheaths, and/or instructions for use.

FIG. 4 illustrates another articulating balloon catheter 110. Articulating balloon catheter 110 is similar to the articulating balloon catheter 10 illustrated in FIGS. 1, 2, 2A, and 3 and described above, except as detailed below. Reference numbers in FIG. 4 refer to the same structural element or feature referenced by the same number in FIGS. 1, 2, 2A, and 3, offset by 100. Thus, articulating balloon catheter 110 comprises a proximal end 112, a distal end 114, an elongate member 116, a first balloon 118, and a second balloon 120.

In the illustrated embodiment, in addition to the infusion port 128, inflation port 130, infusion lumen 132, inflation lumen 134, and guide wire lumen 136, the body 126 of the elongate member 116 defines a second inflation port 185 and a second inflation lumen 186. The second inflation port 185 is disposed on a proximal portion of elongate member 116 and can include any suitable connector and/or adapter capable of attaching one or more devices to elongate member 116, such as those described herein. The second inflation lumen 186 extends from a first opening 187 defined on second inflation port 185 to a second opening 188 defined between the second opening 144 of inflation lumen 134 and the proximal end 164 of the second balloon 120 and near the proximal end 164 of the second balloon 120.

By positioning the second opening 144 of inflation lumen 134 near the distal end 166 of the second balloon 120 and the second opening 188 of the second inflation lumen 186 near the proximal end 164 of the second balloon 120, the second balloon 120 can be inflated in stages such that the distal portion 172 can be inflated independent of the proximal portion 170 and the proximal portion 170 can be inflated independent of the distal portion 172.

Figure 5:
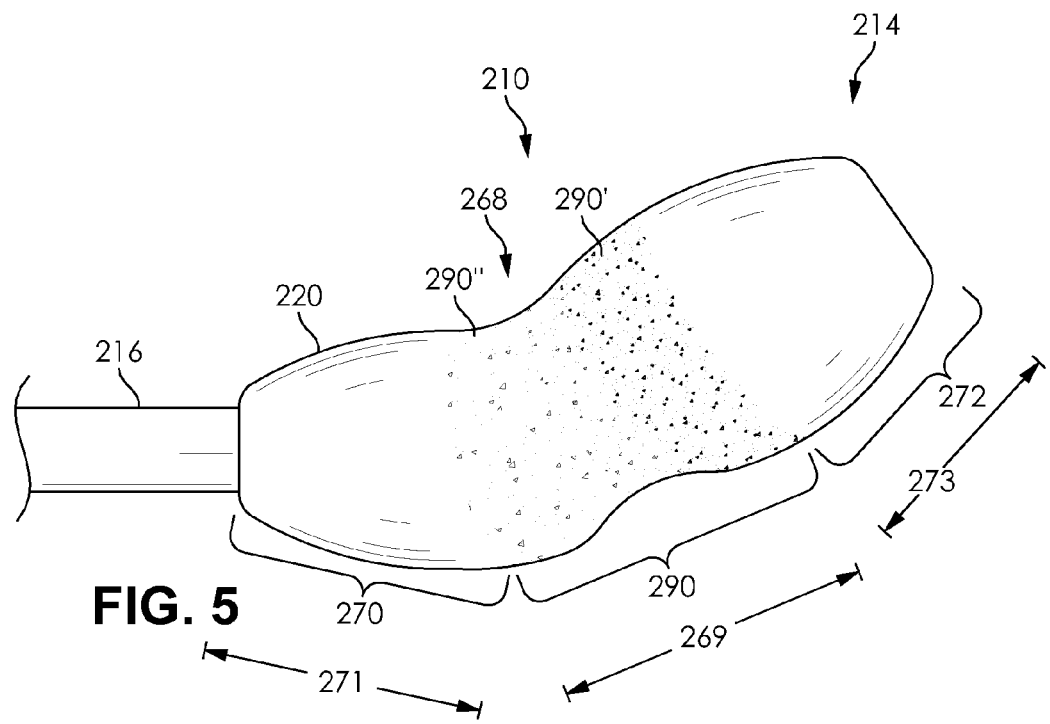
FIG. 5 is a magnified partial side view of the distal end of another articulating balloon catheter.

FIG. 5 illustrates another articulating balloon catheter 210. Articulating balloon catheter 210 is similar to the articulating balloon catheter 10 illustrated in FIGS. 1, 2, 2A, and 3 and described above, except as detailed below. Reference numbers in FIG. 5 refer to the same structural element or feature referenced by the same number in FIGS. 1, 2, 2A, and 3, offset by 200. Thus, articulating balloon catheter 210 comprises a proximal end (not shown), a distal end 214, an elongate member 216, and a balloon 220.

In the illustrated embodiment, the articulating balloon catheter 210 omits the inclusion of a balloon that defines a plurality of pores (e.g., first balloon 18) and elongate member 216 omits the inclusion of an infusion port (e.g., infusion port 28) and an infusion lumen (e.g., infusion lumen 32). Articulating region 268 comprises a processed portion 290 of the balloon 220 such that the material properties of the balloon 220 have been altered along the articulating region 268. In addition, the articulating region 268 has a length 269 that is greater than the length 271 of the proximal portion 270 and the length 273 of the distal portion 272.

Any suitable method can be used to alter the material properties of balloon 220, such as those described herein. In the embodiment illustrated, a solvent has been applied to the articulating region 268 about the entire circumference of balloon 220 such that the articulating region 268 has an elastic modulus that is greater than the elastic modulus of the proximal portion 270 and/or distal portion 272 (e.g., the articulating region 268 is relatively more rigid than the proximal portion 270 and distal portion 272 of the balloon 220). In addition, the material forming the balloon 220 has been processed such that a distal portion 290' of the articulating region 268 has an elastic modulus that is greater than a proximal portion 290" of the articulating region 268 (e.g., the distal portion 290' is relatively more rigid than the proximal portion 290"). This can be accomplished, for example, by altering the material properties of the distal portion 290' of the articulating region 268 using a first process and altering the material properties of the proximal portion 290" of the articulating region 268 using a second process that is different than the first process. For example, the proximal portion 290" of the articulating region 268 can be processed for a first period of time and the distal portion 290' of the articulating region 268 can be processed for a second period of time that is different than the first period of time. The second period of time can be greater than, or less than, the first period of time. Alternatively, the proximal portion of an articulating region can be processed using a first material (e.g., solvent) and the distal portion of the articulating region can be processed using a second material that is different than the first material.

While the articulating region 268 of the balloon 220 has been illustrated as being processed about the entire circumference of the balloon 220, any suitable portion of a balloon can be processed to accomplish an articulating region. Skilled artisans will be able to select a suitable portion of a balloon to process to create an articulating region according to a particular embodiment based on various considerations, including the desired articulation between the proximal portion and the distal portion of a balloon. For example, alternative to processing the articulating region of a balloon about the entire circumference of the balloon, the articulating region of a balloon can be process about a portion of the circumference of a balloon.

While the articulating region 268 of the balloon 220 has been illustrated as having a distal portion 290' that has an elastic modulus that is greater than the elastic modulus of the proximal portion 290" (e.g., the distal portion 290' is relatively more rigid than the proximal portion 290"), an articulating region of a balloon can have any suitable elastic modulus and rigidity along its length. Skilled artisans will be able to select a suitable elastic modulus for the articulating region of a balloon according to a particular embodiment based on various considerations, including the desired articulation between the proximal portion and the distal portion of a balloon. For example, the articulating region of a balloon can have a distal portion that has an elastic modulus (e.g., rigidity) that is greater than, less than, or equal to, the elastic modulus (e.g., rigidity) of a proximal portion. Alternatively, the articulating region can have a proximal portion, an intermediate portion, and a distal portion. The proximal portion can have an elastic modulus (e.g., rigidity) that is greater than, less than, or equal to, the elastic modulus (e.g., rigidity) of the intermediate portion and/or distal portion, the intermediate portion can have an elastic modulus (e.g., rigidity) that is greater than, less than, or equal to, the elastic modulus (e.g., rigidity) of the proximal portion and/or distal portion, and the distal portion can have an elastic modulus (e.g., rigidity) that is greater than, less than, or equal to the elastic modulus (e.g., rigidity) of the proximal portion and/or the intermediate portion.

Figure 6:
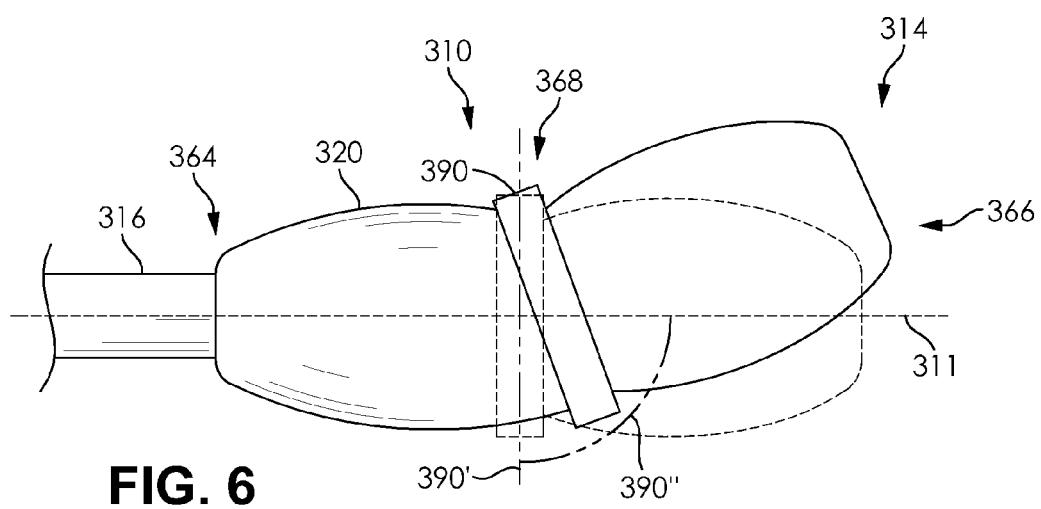
FIG. 6 is a magnified partial side view of the distal end of another articulating balloon catheter.

FIG. 6 illustrates another articulating balloon catheter 310. Articulating balloon catheter 310 is similar to the articulating balloon catheter 210 illustrated in FIG. 5 and described above, except as detailed below. Reference numbers in FIG. 6 refer to the same structural element or feature referenced by the same number in FIG. 5, offset by 100. Thus, articulating balloon catheter 310 comprises a proximal end (not shown), a distal end 314, an elongate member 316, and a balloon 320.

In the illustrated embodiment, alternative to forming the articulating region as a processed portion of a balloon as illustrated in FIG. 5, articulating region 368 comprises a restraining band 390 attached to the exterior surface of the balloon 320. The restraining band 390 is formed of an elastic polymer material and is disposed between the proximal end 364 and the distal end 366 of the balloon 320. The restraining band 390 is disposed on a plane 390' that extends at an angle 390" to the lengthwise axis 311 of articulating balloon catheter 310 when the articulating balloon catheter 310 is in the first configuration. This structural arrangement is shown in phantom lines in FIG. 6. The angle 390" at which the plane 390' extends relative to the lengthwise axis 311 can comprise any suitable angle, and skilled artisans will be able to select a suitable angle to position a plane containing a restraining band relative to the lengthwise axis of an articulating balloon catheter according to a particular embodiment based on various considerations, including the desired inflated configuration of an articulating balloon catheter. Example angles considered suitable include 45 degrees, about 45 degrees, 90 degrees, about 90 degrees, 135 degrees, about 135 degrees, angles that facilitate articulation between the proximal portion and the distal portion of a balloon when the balloon is moved between the deflated and inflated configurations, and any other angle considered suitable for a particular embodiment.

Restraining band 390 can comprise any suitable structural arrangement and be formed of any suitable material. Skilled artisans will be able to select a suitable structural arrangement and material to form a restraining band according to a particular embodiment based on various considerations, including the desired articulation between the proximal portion and the distal portion of a balloon. Example structural arrangements considered suitable include a restraining band that has a constant thickness and/or width along its length, a restraining band that has a thickness and/or width that varies along its length, a restraining band that is formed of the same material along the entirety of its length, a restraining band that is formed of a first material along a first portion of its length and a second material along a second portion of its length that is different than the first material, and any other structural arrangement considered suitable for a particular embodiment. Example materials considered suitable to form a restraining band include, but are not limited to, those described herein, biocompatible materials, materials that can be made biocompatible, compliant materials, metals such as stainless steel, titanium, nickel-titanium alloy (e.g., Nitinol), polymers, Pebax (Pebax is a registered trademark of Ato Chimie Corporation of Allee des Vosges, Courbevoie, France), nylon, polymers, elastic polymers, polyethylene, polyurethane, silicone, coiled materials, braided materials, elastic materials, rigid materials, and any other material considered suitable for a particular embodiment. For example, a restraining band can be formed of a compliant material such that when the balloon is in the inflated configuration, the portion of the balloon disposed under the restraining band is constrained relative to the portions of the balloon that are not disposed under the restraining band.

While a restraining band 390 has been illustrated as attached to the balloon 320, any suitable structure can be disposed on, or attached to, a balloon to accomplish an articulating region as described herein. Skilled artisans will be able to select a suitable structure to include with a balloon to create an articulating region according to a particular embodiment based on various considerations, including the desired amount of articulation between the proximal portion and the distal portion of the balloon. Example structures considered suitable include stents, corrugated materials, and any other structure considered suitable for a particular embodiment.

Figure 7:
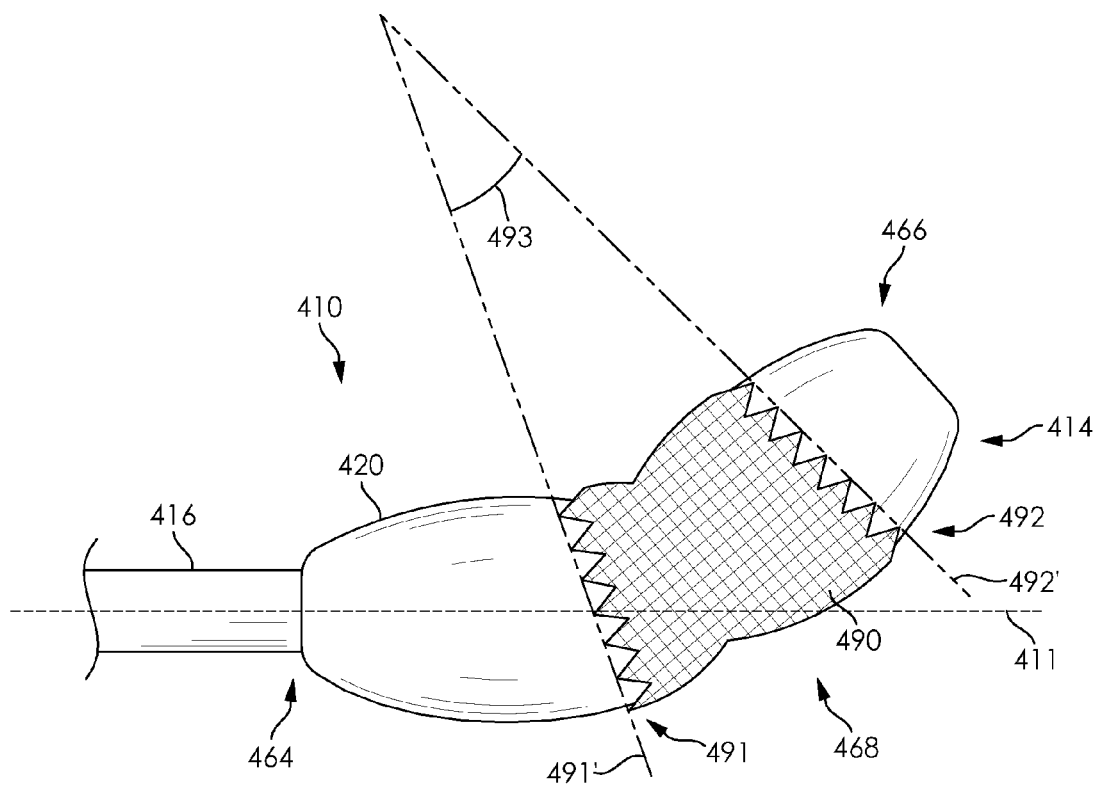
FIG. 7 is a magnified partial side view of the distal end of another articulating balloon catheter.

FIG. 7 illustrates another articulating balloon catheter 410. Articulating balloon catheter 410 is similar to the articulating balloon catheter 210 illustrated in FIG. 5 and described above, except as detailed below. Reference numbers in FIG. 7 refer to the same structural element or feature referenced by the same number in FIG. 5, offset by 200. Thus, articulating balloon catheter 410 comprises a proximal end (not shown), a distal end 414, an elongate member 416, and a balloon 420.

In the illustrated embodiment, alternative to forming the articulating region as a processed portion of a balloon as illustrated in FIG. 5, articulating region 468 comprises a stent 490 attached to the exterior surface of balloon 420. Stent 490 is disposed between the proximal end 464 and the distal end 466 of the balloon 420 and comprises a frame that defines closed cell stent. Stent 490 is formed of a polymeric material, however, a stent can be formed of any suitable material, such as those described herein.

In the embodiment illustrated, stent 490 has a proximal end 491 and a distal end 492. The proximal end 491 is disposed on a first plane 491' and the distal end 492 is disposed on a second plane 492'. The first plane 491' and the second plane 492' are disposed parallel to each other when the balloon 420 is in the deflated configuration and are disposed at angle 493 to one another when the balloon 420 is in the inflated configuration, as shown in FIG. 7. Each of the first plane 491' and second plane 492' is disposed orthogonal to the lengthwise axis 411 of articulating balloon catheter 410 when the balloon 420 is in the deflated configuration. Alternatively, the proximal end and the distal end of a stent, or portions of the proximal end and/or the distal end of a stent, can be disposed on separate planes that are disposed at any suitable angle to one another and/or the lengthwise axis of an articulating balloon catheter when the balloon of the articulating balloon catheter is in the deflated configuration.

While a particular stent has been illustrated, any suitable stent can be used to form an articulating region of a balloon, and skilled artisans will be able to select a suitable stent to include on an articulating balloon catheter according to a particular embodiment based on various considerations, including the structural arrangement at a desired point of treatment. Examples of suitable stents are described herein. Alternative to attaching a stent to the exterior surface of a balloon, as illustrated in FIG. 7, a stent can be disposed within the material that forms a balloon.

Figure 8:
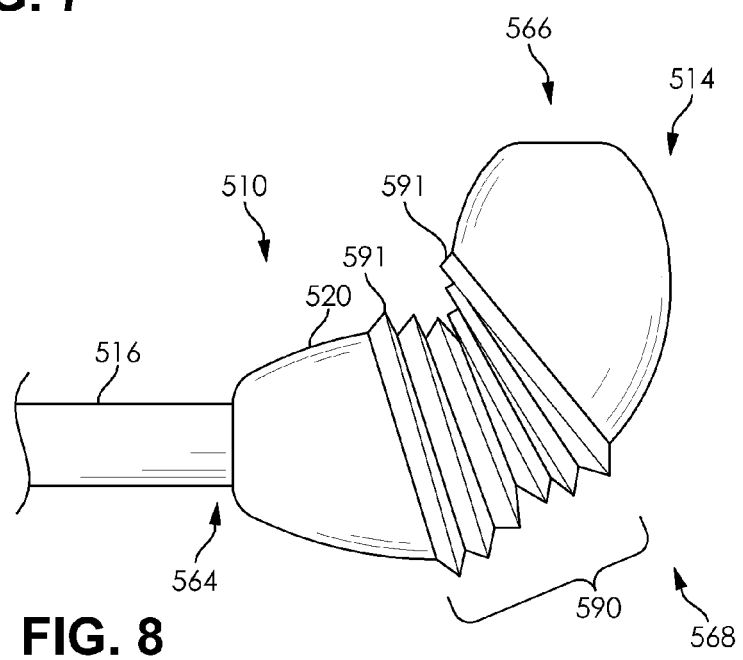
FIG. 8 is a magnified partial side view of the distal end of another articulating balloon catheter.

FIG. 8 illustrates another articulating balloon catheter 510. Articulating balloon catheter 510 is similar to the articulating balloon catheter 210 illustrated in FIG. 5 and described above, except as detailed below. Reference numbers in FIG. 8 refer to the same structural element or feature referenced by the same number in FIG. 5, offset by 300. Thus, articulating balloon catheter 510 comprises a proximal end (not shown), a distal end 514, an elongate member 516, and a balloon 520.

In the illustrated embodiment, alternative to forming the articulating region as a processed portion of a balloon as illustrated in FIG. 5, articulating region 568 comprises a corrugated region 590 of balloon 520 that is formed between the proximal end 564 and the distal end 566 of the balloon 520. The corrugated region 590 comprises a plurality of ridges 591 that extend outward and away from the elongate member 516. Each ridge of the plurality of ridges 591 extends about the entire circumference of balloon 520. Alternatively, a ridge can extend about a portion of the circumference of a balloon.

While corrugated region 590 has been illustrated as formed as a portion of the material that forms balloon 520, a corrugated region can be formed as a separate element attached to the exterior or interior surface of a balloon or disposed within the wall of a balloon. The material that forms the corrugated region of a balloon can be the same as the material that forms the proximal portion and/or distal portion of a balloon, or different than the material that forms the proximal portion and/or distal portion of a balloon. Example methods of achieving a corrugated region 590 are described herein.

While corrugated region 590 has been illustrated as comprising a plurality of ridges 591, the corrugated region of a balloon can be formed of any suitable number of ridges and skilled artisans will be able to select a suitable number of ridges to form a corrugated region of a balloon according to a particular embodiment based on various considerations, including the desired amount of articulation between the proximal portion and the distal portion of the balloon. Example number of ridges considered suitable to form a corrugated region of a balloon include one, at least one, two, a plurality, three, four, five, six, seven, eight, and any other number considered suitable for a particular embodiment.

Any of the elements, features, and/or structural arrangements described herein with respect to any articulating balloon catheter, such as articulating balloon catheter 10, articulating balloon catheter 110, articulating balloon catheter 210, articulating balloon catheter 310, articulating balloon catheter 410, and/or articulating balloon catheter 510, can be combined in any suitable manner. Skilled artisans will be able to select a suitable element, feature, and/or structural arrangement to include in an articulating balloon catheter according to a particular embodiment based on various considerations, such as the structural arrangement at a point of treatment within which an articulating balloon catheter is intended to be used.

Methods of treatment are described herein. While the methods described herein are shown and described as a series of acts, it is to be understood and appreciated that the methods are not limited by the order of acts, as some acts may in accordance with these methods, be omitted, be repeated, or occur in different orders and/or concurrently with other acts described herein.

Figure 9:
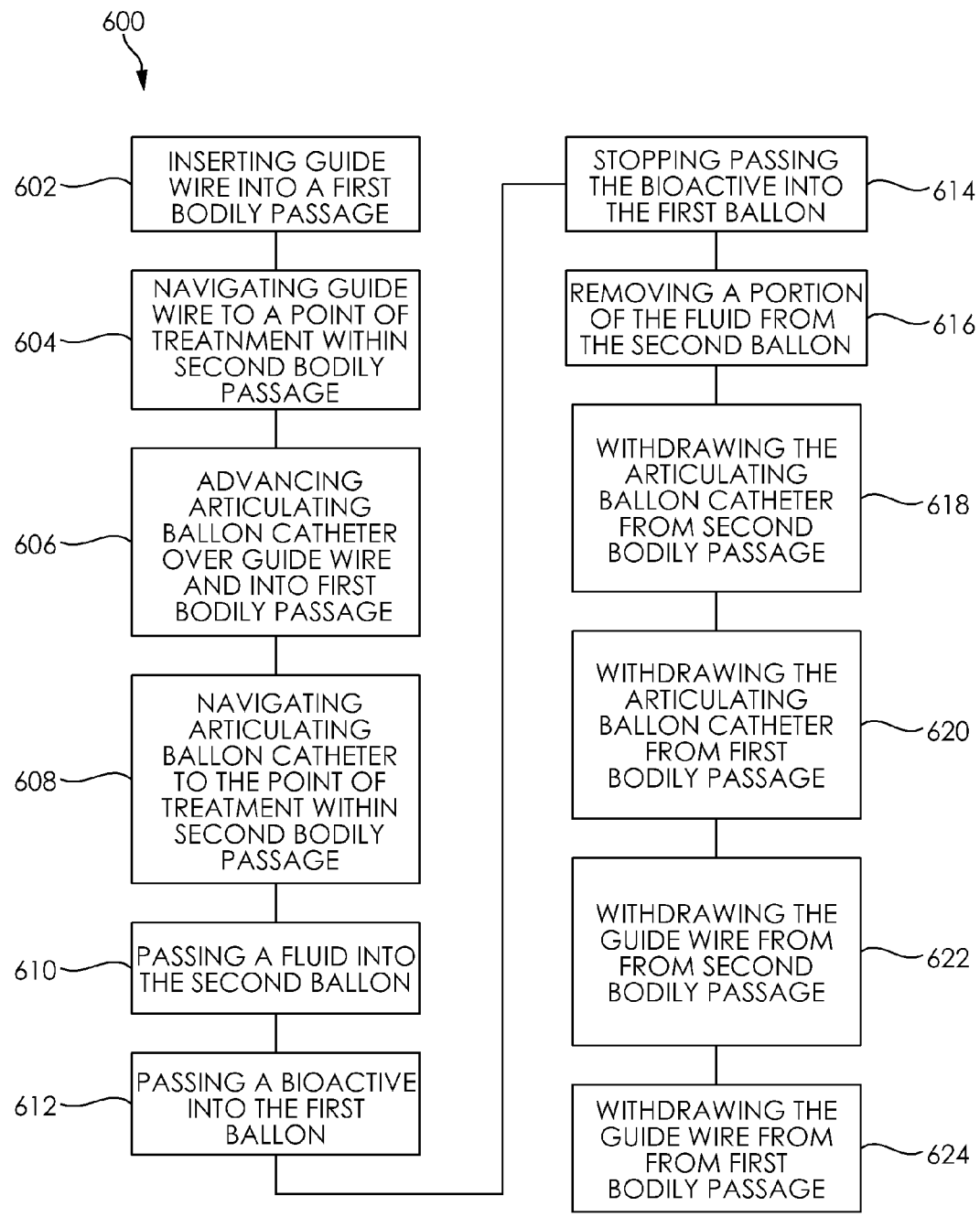
FIG. 9 is a flowchart representation of a method of treatment using an articulating balloon catheter.

FIG. 9 is a flowchart representation of a method of treatment 600 using an articulating balloon catheter.

A step 602 comprises inserting a guide wire having a proximal end and a distal end into a first bodily passage such that the distal end of the guide wire is disposed within a first bodily passage. Another step 604 comprises navigating the distal end of the guide wire to a point of treatment within a second bodily passage in communication with the first bodily passage. The second bodily passage disposed at an angle to the first bodily passage. Another step 606 comprises advancing an articulating balloon catheter having a proximal end and a distal end over the previously placed guide wire such that the distal end of the articulating balloon catheter is disposed within the first bodily passage. Another step 608 comprises navigating the distal end of the articulating balloon catheter to the point of treatment within the second bodily passage such that the proximal portion of the second balloon is disposed within the first bodily passage and the distal portion of the second balloon is disposed within the second bodily passage. Another step 610 comprises passing a fluid (e.g., saline) through an inflation lumen and into an inflation chamber of a second balloon such that the second balloon moves from a deflated configuration to an inflated configuration. Another step 612 comprises passing a bioactive through an infusion lumen into an infusion chamber of the first balloon with a pressure sufficient to expel the bioactive through a pore of a plurality of pores. Another step 614 comprises stopping the step of passing a bioactive through the infusion lumen and into the first balloon. Another step 616 comprises removing a portion of the fluid from the inflation chamber of the second balloon. Another step 618 comprises withdrawing the distal end of the articulating balloon catheter from the second bodily passage. Another step 620 comprises withdrawing the distal end of the articulating balloon catheter from the first bodily passage. Another step 622 comprises withdrawing the distal end of the guide wire from the second bodily passage. Another step 624 comprises withdrawing the distal end of the guide wire from the first bodily passage.

Step 602 can be accomplished by applying a distally-directed force on any suitable portion of the guide wire such that the distal end of the guide wire is disposed within the first bodily passage. Step 602 can be accomplished using a guide wire that has any suitable length, structural configuration, and that is formed of any suitable material.

Step 604 can be accomplished by applying a distally-directed force on any suitable portion of the guide wire such that the distal end of the guide wire is disposed at a point of treatment. Alternatively, step 604 can be accomplished such that the distal end of the guide wire is disposed near, adjacent, proximal to, or distal to a point of treatment. Optionally step 604 can be accomplished using any suitable visualization technique, and skilled artisans will be able to select a suitable visualization technique according to a particular embodiment based on various considerations, including the treatment intended to be performed. Example visualization techniques considered suitable include x-ray, fluoroscopy, ultrasound, direct visualization with a scope, magnetic resonance imaging, and any other visualization technique considered suitable for a particular embodiment. An optional step comprises confirming placement of the distal end of the guide wire using any suitable visualization technique, such as those described herein.

Alternatively, step 604 can comprise navigating the distal end of the guide wire to a point of treatment within the first bodily passage. Optionally, steps 602 and 604 can be omitted in methods that do not require the use of a guide wire. For example, when an elongate member included in an articulating balloon catheter omits the inclusion of a guide wire lumen.

Step 606 can be accomplished by applying a distally-directed force on any suitable portion of an articulating balloon catheter (e.g., elongate member). Step 606 can be accomplished using any suitable articulating balloon catheter, and skilled artisans will be able to select a suitable articulating balloon catheter to use in a method of treatment according to a particular embodiment based on various considerations, including the location of the point of treatment, and/or the type of treatment intended to be performed. Example articulating balloon catheters considered suitable to use in a method of treatment include the articulating balloon catheters described herein, such as articulating balloon catheter 10, articulating balloon catheter 110, articulating balloon catheter 210, articulating balloon catheter 310, articulating balloon catheter 410, articulating balloon catheter 510, variations thereof, and any other articulating balloon catheter considered suitable for a particular method of treatment. An exemplary articulating balloon catheter that can be used to accomplish the methods, steps, alternative steps, and/or optional steps described herein is illustrated and described with respect to FIGS. 1, 2, 2A, and 3, and comprises an elongate member 16, a first balloon 18, and a second balloon 20.

Step 606 can be accomplished by inserting the proximal end of the guide wire through the guide wire lumen 36 defined by the elongate member 16 and applying a distally-directed force on the articulating balloon catheter 10 until the distal end 14 of the articulating balloon catheter 10 is disposed within the first bodily passage.

In embodiments in which a guide wire is not used to complete a method of treatment, an alternative step comprises introducing an articulating balloon catheter into a first bodily passage such that the distal end of the articulating balloon catheter is disposed within the first bodily passage.

Figure 10:
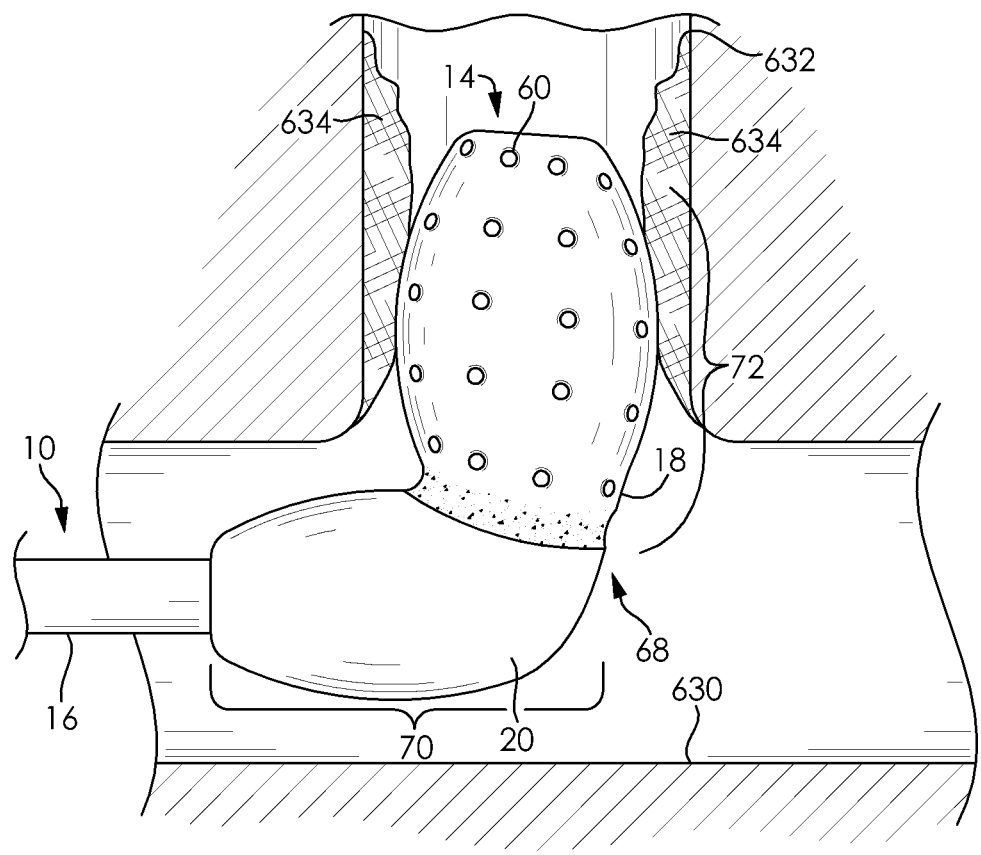
FIG. 10 is a sectional view that illustrates a portion of an articulating balloon catheter disposed within a bodily passage.

Step 608 can be accomplished by applying a distally-directed force on any suitable portion of the articulating balloon catheter 10 such that the distal end 14 of the articulating balloon catheter 10 is disposed at a point of treatment within the second bodily passage. Step 608 is accomplished such that the proximal portion 70 of the second balloon 20 is disposed within the first bodily passage and the distal portion 72 of the second balloon 20 is disposed within the second bodily passage. This is illustrated in FIG. 10, which illustrates the first bodily passage as an artery 630 and the second bodily passage as a vein 632 (e.g., fistula). The vein 632 is illustrated as having a blockage 634, such as a stricture, atherosclerosis, intimal hyperplasia, thrombosis, lesion, or the like. For example, the embodiments described herein can be used to treat failing arteriovenous fistulas and/or grafts.

While step 608 has been described as being completed such that the proximal portion 70 is disposed within the first bodily passage and the distal portion 72 is disposed within the second bodily passage, any suitable portion of a balloon can be disposed within the first bodily passage and/or second bodily passage. Skilled artisans will be able to select a suitable portion of a balloon to position in a bodily passage according to a particular embodiment based on various considerations, including the treatment intended to be performed. For example, a portion, or the entirety, of the proximal portion, articulating region, and/or distal portion of a balloon can be disposed within a first bodily passage and/or a second bodily passage that is in communication with the first bodily passage.

Alternatively, step 608 can be accomplished such that the distal end 14 of the articulating balloon catheter 10 is disposed near, proximal to, or distal to a point of treatment. Optionally step 608 can be accomplished using any suitable visualization technique, such as those described herein. For example, an optional step that can be completed concurrently with, or subsequent to, the step of navigating the distal end of the articulating balloon catheter to a point of treatment within the second bodily passage comprises confirming placement of the articulating balloon catheter within the bodily passage such that a balloon of the articulating balloon catheter is disposed adjacent to, or substantially adjacent to, proximal to, distal to, or near, the point of treatment. This optional step can be accomplished using any suitable visualization technique, such as those described herein. In embodiments in which one or more markers have been included on the articulating balloon catheter, another optional step comprises locating the one or markers. Another optional step comprises determining if the location of the one or more markers relative to the point of treatment is acceptable to perform the treatment. If the position of the one or more markers is not acceptable, then another optional step comprises continuing to navigate the articulating balloon catheter to the point of treatment. This can be accomplished by applying a proximally-directed force or a distally-directed force on any suitable portion of the articulating balloon catheter such that the position of the distal end of the articulating balloon catheter relative to the point of treatment is acceptable to perform treatment. Another optional step comprises repeating the steps of locating the one or more markers, determining if the location of the one or more markers relative to the point of treatment is acceptable, and/or continuing to navigate the articulating balloon catheter to the point of treatment.

Alternatively, step 608 can comprise navigating the distal end 14 of the articulating balloon catheter 10 to a point of treatment within the first bodily passage. Optionally, step 604 and step 608 can be accomplished concurrently.

Step 610 can be accomplished by introducing a fluid into the inflation chamber to advance the second balloon 20 from the deflated configuration to the inflated configuration. This is illustrated in FIG. 10 in which the structural arrangement of the articulating balloon catheter 10 facilitates the articulating balloon catheter 10 responding to the anatomy of the bodily passage(s). The amount of the exterior surface of the first balloon 18 and/or the second balloon 20 that contacts the wall of the first bodily passage and/or second bodily passage, and the amount of pressure exerted by the exterior surface of the first balloon 18 and/or the second balloon 20 onto the wall of the first bodily passage and/or second bodily passage, will depend on the amount fluid passed into the inflation chamber of the second balloon. For example, the second balloon can be inflated with a pressure sufficient such that a portion, the entirety, or a majority, of the first balloon and/or second balloon contacts the wall of the first bodily passage and/or second bodily passage. Depending on the embodiment used to complete the steps described herein, step 610 can be accomplished such that the distal portion 72 articulates relative to the proximal portion 70.

Example fluids considered suitable to introduce into an inflation chamber to advance the second balloon 20 to an inflated configuration include, but are not limited to, saline, water, contrast, or a mixture of one or more of saline, water, and/or contrast.

Optionally, step 610 can be accomplished such that the distal portion of the second balloon moves from the deflated configuration to the inflated configuration and the proximal portion remains in the deflated configuration.

Alternatively, in embodiments in which the elongate member defines a first inflation lumen and a second inflation lumen, an alternative step that can be completed comprises introducing a fluid into the inflation chamber through the first inflation lumen and another step comprises introducing a fluid into the inflation chamber through the second inflation lumen. These alternative steps can be accomplished concurrently, or separate from one another.

Step 612 can be accomplished by passing a bioactive through the infusion lumen such that it is passed through the infusion chamber and a pore of the plurality of pores 60. The bioactive can be passed into the infusion lumen using any suitable device (e.g., a syringe in communication with the infusion lumen). Step 612 can be accomplished concurrently with step 610 (e.g., while second balloon 20 is in the inflated configuration), or subsequent to step 616 (e.g., while second balloon 20 is in the deflated configuration). As described herein, each pore of the plurality of pores 60 permits bioactive to pass through the pore (e.g., with the application of pressure within the infusion chamber). Depending on the size and number of pores defined by the wall of the first balloon 18, the bioactive can be introduced into a bodily passage, or infused into the wall of a bodily passage, at a variety of rates, or such that the bioactive is passed through a pore of the plurality of pores 60, a portion of the plurality of pores 60, a set of pores of the plurality of pores 60, or each pore of the plurality of pores 60.

Any suitable bioactive can be used in accordance with the embodiments described herein, and skilled artisans will be able to select a suitable bioactive according to a particular embodiment based on various considerations, including the treatment intended to be performed. Example bioactives considered suitable include those described herein, anti-proliferatives, such as paclitaxel, anti-inflammatories, such as dexamethasone, anti-microbials, agents, anticlotting agents, therapeutic agents, and any other substance considered suitable for a particular embodiment. For example, the use of an anti-proliferative, such as paclitaxel, can be used to inhibit the progression of neointimal hyperplasia and/or an anti-inflammatory, such as dexamethasone, can be used to limit the recurrence of thrombosis formation.

Step 614 can be accomplished by stopping the step of passing a bioactive through infusion lumen 32 and into the infusion chamber. When a syringe is being used to pass the bioactive into the infusion lumen, this can be accomplished by removing the distally-directed force being applied to the plunger of the syringe.

In embodiments that omit the inclusion of a first balloon, steps 612 and 614 can be omitted. An alternative step that can be completed comprises delivering a device at the point of treatment. The device can be disposed on the distal portion, or a portion of the distal portion, of the balloon of an articulating balloon catheter and can comprise any suitable device such as a stent, mechanically expandable stent, and/or graft. This step can be accomplished as described above with respect to step 610.

Step 616 can be accomplished by removing a portion of the fluid passed into the inflation chamber. For example, a syringe in communication with the inflation lumen can be used to apply vacuum pressure to remove the fluid from the inflation chamber. This can be accomplished by applying a proximally-directed force on the plunger of the syringe. The amount of fluid removed from inflation chamber can vary depending on the procedure. For example, alternative to removing a portion of the fluid, all of the fluid, or as much as possible, can be removed from inflation chamber.

Step 618 can be accomplished by applying a proximally-directed force on any suitable portion of the articulating balloon catheter 10 (e.g., elongate member 16) such that it is advanced proximally over the guide wire and the distal end 14 is completely removed from the second bodily passage. Alternatively, if the distal end of the articulating balloon catheter has been navigated to a point of treatment independent of a guide wire, the step of withdrawing the distal end of the articulating balloon catheter from the bodily passage can be accomplished by applying a proximally-directed force on any suitable portion of the articulating balloon catheter until the distal end articulating balloon catheter is completely removed from the second bodily passage. Optionally, step 618 can be omitted in methods in which the point of treatment is disposed within a first bodily passage.

Step 620 can be accomplished by applying a proximally-directed force on any suitable portion of the articulating balloon catheter 10 (e.g., elongate member 16) such that it is advanced proximally over the guide wire and the distal end 24 is completely removed from the first bodily passage. Alternatively, if the distal end of the articulating balloon catheter has been navigated to a point of treatment independent of a guide wire, the step of withdrawing the distal end of the articulating balloon catheter from the bodily passage can be accomplished by applying a proximally-directed force on any suitable portion of the articulating balloon catheter until the distal end articulating balloon catheter is completely removed from the first bodily passage.

Step 622 can be accomplished by applying a proximally-directed force on any suitable portion of the guide wire such that it is advanced proximally and is completely removed from the second bodily passage. Optionally, this step can be accomplished in combination with step 618. Optionally, step 622 can be omitted in methods in which the inclusion of a guide wire has been omitted or in methods in which the point of treatment is disposed within a first bodily passage.

Step 624 can be accomplished by applying a proximally-directed force on any suitable portion of the guide wire such that it is advanced proximally and is completely removed from the first bodily passage. Optionally, this step can be accomplished in combination with step 620. Optionally, step 624 can be omitted in methods in which the inclusion of a guide wire has been omitted.

While the various steps, alternative steps, and optional steps have been described above with respect to a method of treating a first bodily passage that comprises an artery and a second bodily passage that comprises a vein, these steps, alternative steps, and optional steps can be accomplished with respect to treating any suitable bodily passage, or bodily passages, including, but not limited to, veins, arteries, fistulas, grafts, and/or the wall and/or tissue of each of these bodily passages. In addition, these steps, alternative steps, and optional steps can be used with respect to treating any suitable condition, including vascular strictures, atherosclerosis, intimal hyperplasia, thrombosis, lesions, failing arteriovenous fistulas, failing arteriovenous grafts, or any other condition in which the articulating balloon catheter and/or methods described herein would be considered suitable.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A medical device comprising:
an elongate member having an elongate member proximal end, an elongate member distal end, and an elongate member body that defines an inflation lumen; and
a balloon attached to the elongate member and adapted to move between a deflated configuration and an inflated configuration, the balloon comprising a balloon proximal end, a balloon distal end, an articulating region disposed between the balloon proximal end and the balloon distal end, a proximal portion extending from the balloon proximal end to the articulating region, a distal portion extending from the articulating region to the balloon distal end, and a balloon wall that defines an inflation chamber in communication with the inflation lumen, the articulating region configured to provide articulation between the proximal portion and the distal portion of the balloon, the articulating region formed of a first material, the proximal portion formed of a second material, and the distal portion formed of a third material, the first material being relatively more rigid than the second material and the third material.

2. The medical device of claim 1, wherein the elongate member body defines an infusion lumen; and
further comprising a second balloon attached to the elongate member and adapted to move between a deflated configuration and an inflated configuration, the second balloon positioned over a portion of the balloon and comprising a second balloon proximal end, a second balloon distal end, and a second balloon wall that defines a pore and an infusion chamber in communication with the infusion lumen, the pore extending through the second balloon wall and providing access to the infusion chamber.

3. The medical device of claim 2, wherein the second balloon proximal end is attached to the balloon distal to the articulating region.

4. The medical device of claim 1, wherein the articulating region comprises a portion of the balloon that has been processed with a solvent or bombarded with an ion beam.

5. The medical device of claim 1, wherein the articulating region comprises at least one of a restraining band or a stent disposed about the circumference of the balloon.

6. The medical device of claim 1, wherein the articulating region comprises a corrugated region that defines a plurality of ridges.

7. The medical device of claim 1, wherein the elongate member body defines an inflation port, a first opening in communication with the inflation lumen, and a second opening in communication with the inflation lumen, the first opening defined on the inflation port, the second opening defined between the balloon distal end and the articulating region.

8. The medical device of claim 7, wherein the elongate member body defines a third opening in communication with the inflation lumen, the third opening defined between the second opening and the balloon proximal end.

9. The medical device of claim 1, wherein the balloon is formed of a material that has a rated burst pressure between about 15 ATM and about 30 ATM.

10. The medical device of claim 1, wherein the balloon is formed of a textile balloon.

11. A medical device comprising:
an elongate member having an elongate member proximal end, an elongate member distal end, and an elongate member body that defines an inflation lumen; and
a first balloon attached to the elongate member and adapted to move between a deflated configuration and an inflated configuration, the first balloon comprising a first balloon proximal end, a first balloon distal end, an articulating region disposed between the first balloon proximal end and the first balloon distal end, a proximal portion extending from the first balloon proximal end to the articulating region, a distal portion extending from the articulating region to the first balloon distal end, and a first balloon wall that defines an inflation chamber in communication with the inflation lumen, the articulating region configured to provide articulation between the proximal portion and the distal portion of the first balloon, the articulating region formed of a first material, the proximal portion formed of a second material, and the distal portion formed of a third material, the first material being relatively more rigid than the second material and the third material; and
a second balloon attached to the elongate member and adapted to move between a deflated configuration and an inflated configuration, the second balloon positioned over a portion of the first balloon and comprising a second balloon proximal end, a second balloon distal end, and a second balloon wall that defines a pore and an infusion chamber in communication with the infusion lumen, the pore extending through the second balloon wall and providing access to the infusion chamber.

12. The medical device of claim 11, wherein the second balloon proximal end is attached to the first balloon distal to the articulating region.

13. The medical device of claim 11, wherein the articulating region comprises a portion of the first balloon that has been processed with a solvent or bombarded with an ion beam.

14. The medical device of claim 11, wherein the articulating region comprises at least one of a restraining band or a stent disposed about the circumference of the first balloon.

15. The medical device of claim 11, wherein the articulating region comprises a corrugated region that defines a plurality of ridges.

16. The medical device of claim 11, wherein the elongate member body defines an inflation port, a first opening in communication with the inflation lumen, and a second opening in communication with the inflation lumen, the first opening defined on the inflation port, the second opening defined between the first balloon distal end and the articulating region.

17. The medical device of claim 16, wherein the elongate member body defines a third opening in communication with the inflation lumen, the third opening defined between the second opening and the first balloon proximal end.

18. The medical device of claim 11, wherein the first balloon is formed of a material that has a rated burst pressure between about 15 ATM and about 30 ATM.

19. The medical device of claim 11, wherein the first balloon is formed of a textile balloon.

20. A medical device comprising:
an elongate member having an elongate member proximal end, an elongate member distal end, and an elongate member body that defines an inflation lumen; and
a first balloon attached to the elongate member and adapted to move between a deflated configuration and an inflated configuration, the first balloon comprising a first balloon proximal end, a first balloon distal end, an articulating region disposed between the first balloon proximal end and the first balloon distal end, a proximal portion extending from the first balloon proximal end to the articulating region, a distal portion extending from the articulating region to the first balloon distal end, and a first balloon wall that defines an inflation chamber in communication with the inflation lumen, the articulating region configured to provide articulation between the proximal portion and the distal portion of the first balloon, the articulating region formed of a first material, the proximal portion formed of a second material, and the distal portion formed of a third material, the first material being relatively more rigid than the second material and the third material; and a second balloon attached to the elongate member and adapted to move between a deflated configuration and an inflated configuration, the second balloon positioned over a portion of the first balloon and comprising a second balloon proximal end, a second balloon distal end, and a second balloon wall that defines a pore and an infusion chamber in communication with the infusion lumen, the second balloon proximal end attached to the first balloon distal to the articulating region, the pore extending through the second balloon wall and providing access to the infusion chamber.

\* \* \* \* \*